United States Patent
Farazi et al.

(10) Patent No.: US 7,403,813 B1
(45) Date of Patent: *Jul. 22, 2008

(54) SYSTEMS AND METHODS FOR DETECTION OF VT AND VF FROM REMOTE SENSING ELECTRODES

(75) Inventors: Taraneh Ghaffari Farazi, San Jose, CA (US); Gene A. Bornzin, Simi Valley, CA (US); Anders Bjorling, Jarfalla (SE); Yelena Nabutovsky, Mountain View, CA (US); Kjell Noren, Solna (SE)

(73) Assignee: Pacesetter, Inc., Sylmar, CA (US)

( * ) Notice: Subject to any disclaimer, the term of this patent is extended or adjusted under 35 U.S.C. 154(b) by 249 days.

This patent is subject to a terminal disclaimer.

(21) Appl. No.: 10/998,026

(22) Filed: Nov. 24, 2004

(51) Int. Cl.
*A61B 5/0468* (2006.01)
(52) U.S. Cl. .................................... 600/515
(58) Field of Classification Search ................. 600/515
See application file for complete search history.

(56) References Cited

U.S. PATENT DOCUMENTS

| | | | |
|---|---|---|---|
| 4,686,988 A | 8/1987 | Sholder | 128/419 PT |
| 4,708,142 A | 11/1987 | DeCote, Jr. | 128/419 PT |
| 4,712,555 A | 12/1987 | Thornander et al. | 128/419 PG |
| 4,729,376 A | 3/1988 | DeCote, Jr. | 128/419 PT |
| 4,766,902 A * | 8/1988 | Schroeppel | 607/9 |
| 4,788,980 A | 12/1988 | Mann et al. | 128/419 PG |
| 4,809,697 A | 3/1989 | Causey, III et al. | 128/419 PT |
| 4,907,593 A * | 3/1990 | Rapach et al. | 607/19 |
| 4,940,052 A | 7/1990 | Mann et al. | 128/419 PG |
| 4,944,298 A | 7/1990 | Sholder | 128/419 PG |
| 4,944,299 A | 7/1990 | Silvian | 128/419 PG |
| 4,969,467 A | 11/1990 | Callaghan et al. | 128/419 PG |
| 5,040,534 A | 8/1991 | Mann et al. | 128/419 PG |
| 5,313,953 A | 5/1994 | Yomtov et al. | 128/696 |
| 5,350,410 A | 9/1994 | Kleks et al. | 607/28 |
| 5,405,363 A | 4/1995 | Kroll et al. | 607/5 |
| 6,275,734 B1 | 8/2001 | McClure et al. | 607/27 |
| 6,409,675 B1 | 6/2002 | Turcott | 600/508 |

(Continued)

FOREIGN PATENT DOCUMENTS

EP          0578748 B1        5/1996

(Continued)

OTHER PUBLICATIONS

NonFinal Office Action, mailed Aug. 6, 2007: Related U.S. Appl. No. 10/998,027.

(Continued)

*Primary Examiner*—Mark W Bockelman
*Assistant Examiner*—Eric D Bertram

(57) ABSTRACT

Methods and systems are provided for performing ventricular arrhythmia monitoring using at least two sensing channels that are each associated with different sensing vectors, for example by different pairs of extracardiac remote sensing electrodes. Myopotential associated with each of the sensing channels in monitored, and a ventricular arrhythmia monitoring mode is selected based thereon (e.g., based on determined myopotential levels). Ventricular arrhythmia monitoring is then performed using the selected monitoring mode. This description is not intended to be a complete description of, or limit the scope of, the invention. Other features, aspects, and objects of the invention can be obtained from a review of the specification, the figures, and the claims.

9 Claims, 18 Drawing Sheets

U.S. PATENT DOCUMENTS

| | | | |
|---|---|---|---|
| 6,466,821 B1 | 10/2002 | Pianca et al. | 607/18 |
| 6,477,406 B1* | 11/2002 | Turcott | 600/518 |
| 6,491,639 B1 | 12/2002 | Turcott | 600/508 |
| 6,527,729 B1 | 3/2003 | Turcott | 600/528 |
| 6,625,493 B2 | 9/2003 | Kroll et al. | 607/17 |
| 6,658,292 B2 | 12/2003 | Kroll et al. | 607/19 |
| 7,027,858 B2 | 4/2006 | Cao et al. | |
| 2002/0165587 A1* | 11/2002 | Zhang et al. | 607/28 |
| 2003/0097153 A1 | 5/2003 | Bardy et al. | 607/5 |
| 2003/0171661 A1* | 9/2003 | Tong | 600/300 |
| 2003/0204215 A1* | 10/2003 | Gunderson et al. | 607/27 |
| 2004/0230243 A1* | 11/2004 | Haefner et al. | 607/27 |
| 2005/0119708 A1 | 6/2005 | Haefner | 607/17 |

FOREIGN PATENT DOCUMENTS

| | | |
|---|---|---|
| EP | 0941695 B1 | 11/2003 |
| WO | WO 03/039668 A1 | 5/2003 |

OTHER PUBLICATIONS

Notice of Allowance, mailed Jan. 8, 2008: Related U.S. Appl. No. 10/998,027.

* cited by examiner time (arbitrary units)

SYSTEMS AND METHODS FOR DETECTION OF VT AND VF FROM REMOTE SENSING ELECTRODES

CROSS-REFERENCE TO RELATED APPLICATIONS

This application is related to copending U.S. patent application Ser. No. 10/998,027, titled "Systems and Methods for Detection of VT and VF from Remote Sensing Electrodes", filed Nov. 24, 2004.

FIELD OF THE INVENTION

Embodiments of present invention relate to detecting R-waves, monitoring myopotential, detecting levels of myopotential, as well as detecting and treating cardiac arrhythmias.

BACKGROUND

Ventricular arrhythmias include ventricular tachycardia (VT) and ventricular fibrillation (VF). A tachycardia is a fast heart rate (usually over 100 beats per minute) typically caused by disease or injury. It can also be part of a normal response to increased activity or oxygen demands. The average heart beats between 60 and 100 times per minute. When the tachycardia is due to disease or injury, it usually requires treatment. Tachycardias may begin in the upper chambers of the heart (the atria) or the lower chambers of the heart (the ventricles). A ventricular tachycardia (VT) begins in the ventricles. Some are harmless, but others are life threatening in that they can quickly deteriorate to a ventricular fibrillation.

A ventricular fibrillation (VF) is a very fast, chaotic heart rate (usually over 300 beats per minute) in the lower chambers of the heart, resulting from multiple areas of the ventricles attempting to control the heart's rhythm. VF can occur spontaneously (generally caused by heart disease) or when VT has persisted too long. When the ventricles fibrillate, they do not contract normally, so they cannot effectively pump blood. The instant VF begins, effective blood pumping stops. VF quickly becomes more erratic, resulting in sudden cardiac arrest. This arrhythmia must be corrected immediately via a shock from an external defibrillator or an implantable cardioverter defibrillator (ICD). The defibrillator stops the chaotic electrical activity and restores normal heart rhythm.

Appropriate detection of ventricular arrhythmias (requiring high voltage therapy) and discrimination of supraventricular arrhythmias (not requiring high voltage therapy) in a noisy signal is challenging and of great importance, particularly as it relates to an implanted defibrillator using subcutaneous extracardiac electrodes or an external defibrillator. Since such signals are composed of both cardiac and skeletal myopotentials, motion artifacts, electromagnetic interference (EMI), etc., appropriate detection of arrhythmias relies heavily on accurate detection of each subcomponent of such composite signals. There is a need for improved methods and systems that can detect ventricular arrhythmias and discriminate between the different types of arrhythmias even when myopotentials and motion artifacts affect that cardiac signal that is being monitored.

Sensing cardiac electrical activity from electrodes spatially removed from the heart, as in a surface ECG or in a subcutaneous extracardiac configuration is challenging. Non-cardiac signals such as skeletal myopotential and motion artifact can easily be mistaken for an arrhythmia, which can lead to inappropriate therapy. Given the composite nature of subcutaneous signals, it is useful that a scheme for detecting non-cardiac events allow for changes (e.g., daily or hourly) in signal characteristics.

SUMMARY

Some embodiments described herein are directed to methods and systems for monitoring myopotential that may be present in a sensed cardiac signal. More specifically, a cardiac signal is sensed using a pair of extracardiac remote sensing electrodes corresponding to a sensing vector. The cardiac signal is sampled to produce a plurality of samples that are representative of a window of the cardiac signal, and the myopotential is monitored based on the plurality of samples. Methods and systems are also provided for how and when the parameters (e.g., ratio thresholds, line slope thresholds, bin edges, etc.) that are used for monitoring myopotential are updated. Such parameters, which may track changes in cardiac signal trends, can be used for assigning myopotential levels.

Embodiments of the present invention are also directed to methods and systems for performing ventricular arrhythmia monitoring using at least two sensing channels that are each associated with a different pair of extracardiac remote sensing electrodes. In accordance with an embodiment, myopotential associated with at least two sensing channels is monitored, and then a ventricular arrhythmia monitoring mode is selected based on the monitored myopotential. Ventricular arrhythmia monitoring modes include, for example, a single channel sensing mode and a dual channel sensing mode. Ventricular arrhythmia monitoring is then performed using the selected monitoring mode. In accordance with an embodiment of the present invention, thresholding is used to detect R-waves and heart rate if there is at least one channel having a low myopotential level. Then a diagnosis can be made based on the results of the thresholding. If two channels have a medium myopotential level, then those two channels are both monitored so that match filtering or sliding window correlation can be used to detect R-waves and heart rate, thereby allowing for a diagnosis to be made. If no channel has a low myopotential level, and two channels do not have a medium myopotential level, then it is assumed that the somewhat high myopotential levels are due to a patient's normal activity, and thus that the patient is not experiencing a ventricular arrhythmia.

This description is not intended to be a complete description of, or limit the scope of, the invention. Other features, aspects, and objects of the invention can be obtained from a review of the specification, the figures, and the claims.

DETAILED DESCRIPTION

The following description is of the best modes presently contemplated for practicing various embodiments of the present invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Before going into specific details regarding the various embodiments of the present invention, it is first useful to describe an exemplary extracardiac/extravascular defibrillation system, and an exemplary ECG signal.

Overview of Extracardiac/Extravascular Defibrillation System

Figure 1:
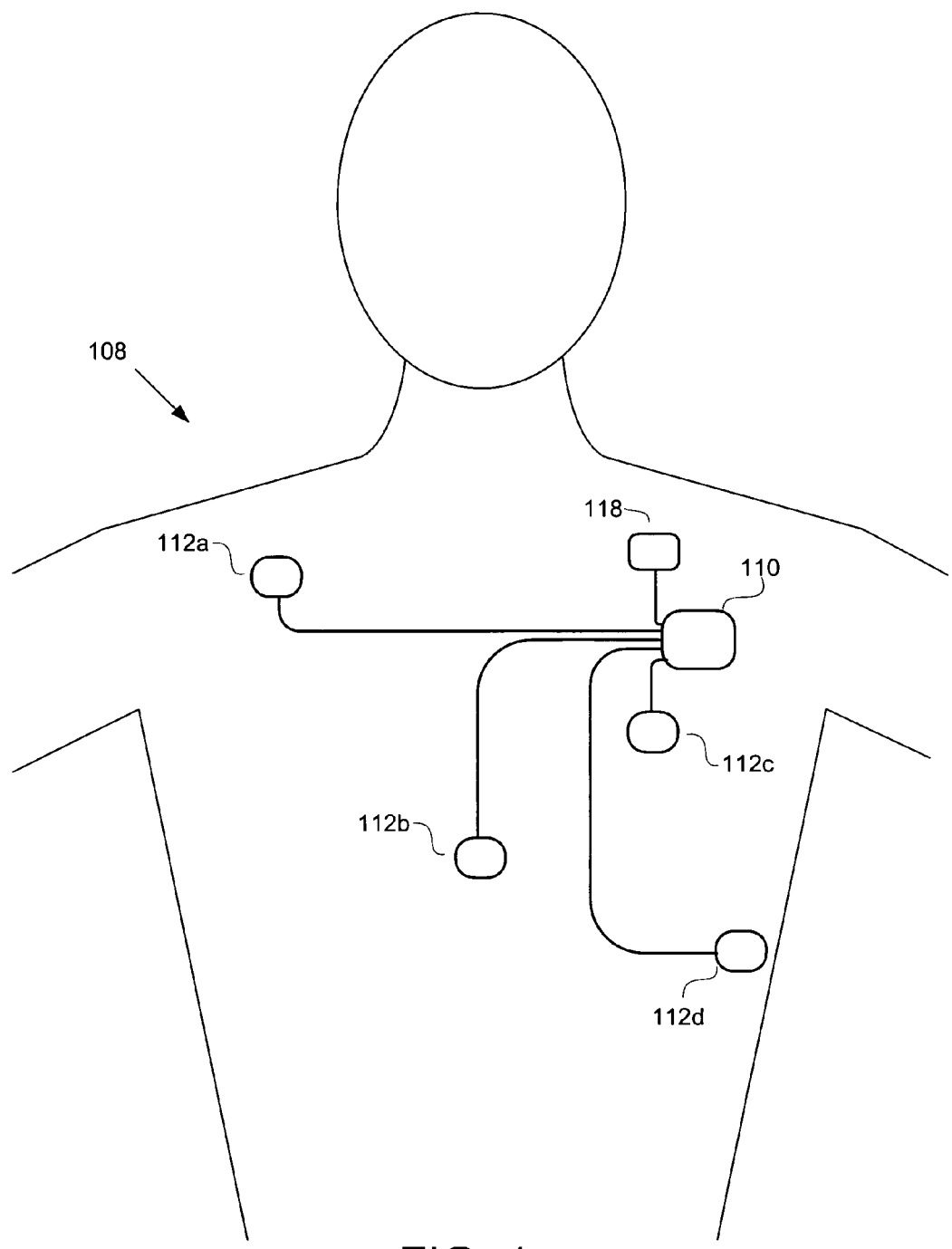
FIG. 1 illustrates components of an exemplary extracardiac/extravascular cardiac stimulation system in which embodiments of the present invention can be useful.

Referring first to FIG. 1, an exemplary extracardiac defibrillation system 108 includes a subcutaneous (subQ) stimulation device 110 and multiple subQ extracardiac electrodes 112 (also referred to as remote sensing electrodes) for detecting electrical cardiac signals within the chest of the patient. The subQ extracardiac electrodes 112 are preferably extravascular and can be, e.g., paddle electrodes or coil electrodes mounted subcutaneously outside of the rib cage, but are not limited thereto. Exemplary locations of the subQ extracardiac electrodes 112 include near the bottom of the sternum (slightly to the left), below the left pectoral area, and below the clavicle and on the back left side (just below the shoulder blade). Of course, additional and/or alternative locations for subQ electrodes 112 are within the scope of the present invention.

The subQ stimulation device 110 can be an implantable cardioverter defibrillator (ICD) and/or a pacemaker. Additional details of the subQ stimulation device 110 are discussed below with reference to FIG. 3.

A non-cardiac patient parameter detector 118 is also shown, which may be, for example, a respiration detector, heart sound detector, motion detector, pulse pressure detector or other detector capable of detecting some non-cardiac-electrical-signal parameter, i.e. a parameter that is not derived from an analysis of cardiac electrical signals. While the non-cardiac patient parameter detector 118 is shown in FIG. 1 as being external to the housing of the stimulation device 110, it is also within the scope of the present invention that the non-cardiac parameter detector 118 can be located within the housing (also known as "can") of the device 110. An exemplary non-cardiac parameter detector 118 is described in U.S. patent application Ser. No. 10/439,615 to Fayram et al., entitled "Optional Use of a Lead for a Unitary Subcutaneous Implantable Cardioverter-Defibrillator," which is incorporated by reference herein. Other exemplary extracardiac detectors/sensors are described in the following patents to Turcott: U.S. Pat. No. 6,409,675 entitled "Extravascular Hemodynamic Monitor"; U.S. Pat. No. 6,527,729 entitled "Method for Monitoring Patient Using Acoustic Sensor"; U.S. Pat. No. 6,491,639 entitled "Extravascular Hemodynamic Sensor"; and U.S. Pat. No. 6,477,406 entitled "Extravascular Hemodynamic Acoustic Sensor", each of which is incorporated by reference herein. Other types of non-cardiac parameter detectors are also within the spirit and scope of the present invention.

In accordance with specific embodiments of the present invention discussed below, the non-cardiac patient parameter detector 118 is used to detect activity of the patient (e.g., whether the patient is active or not). The following patents, which are each incorporated herein by reference, describe exemplary activity sensors that can be used to implement the non-cardiac patient parameter detector 118: U.S. Pat. No. 6,658,292 to Kroll et al., entitled "Detection of Patient's Position and Activity Status using 3 D Accelerometer-Based Position Sensor"; U.S. Pat. No. 6,625,493 to Kroll et al., entitled "Orientation of Patient's Position Sensor using External Field"; and U.S. Pat. No. 6,466,821 to Pianca et al., entitled "AC/DC Multi-Axis Accelerometer for Determining Patient Activity and Body Position."

The particular locations of the implanted components shown in FIG. 1 are merely illustrative and may not necessarily correspond to actual implant locations. In general, any of the components can be implanted in any location that is effective for its intended purposes with, preferably, all components being implanted extracardially and extravascularly.

As will be described below, in accordance with embodiments of the present invention, one or more pairs of the subQ electrodes 112 are used to detect myopotential and/or R-waves. These electrodes can also be used to detect and treat ventricular tachycardias (VT) and ventricular fibrillation (VF), as will also be described below.

Although a system is illustrated wherein subQ electrodes 112 are provided, many embodiments of the present invention would also work using surface electrodes, e.g., of an external automatic defibrillator.

Various components can be separated or combined, as needed. For example, the non-cardiac parameter detector 118, depending upon the parameters to be detected, can be incorporated within the subQ stimulation device 110 (as mentioned above) or within an electrical signal sensor. In addition, the non-cardiac parameter detector 118 can be configured so as to detect a single parameter or some combination of parameters. The system of FIG. 1 is merely exemplary. Exemplary signal transmission lines for interconnecting the various components are shown in FIG. 1. However, other lines or wireless signal transmission may alternatively be employed.

Exemplary ECG Waveform

Figure 2:
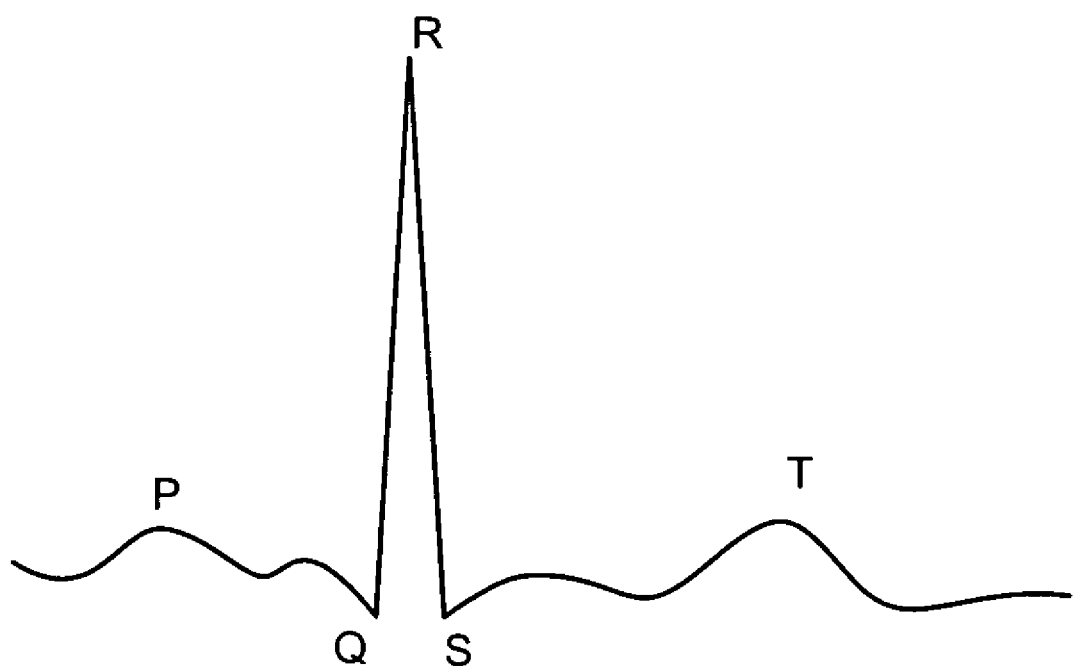
FIG. 2 illustrates a portion of an exemplary ECG waveform.

Referring now to FIG. 2, a graphic representation of a typical electrocardiogram (ECG) waveform is provided, with the conventional nomenclature for the various portions thereof shown. The beginning of a heart beat is initiated by a P wave which is normally a small positive wave. Following the P wave there is an ECG waveform portion which is substantially constant in amplitude. This substantially constant portion will have a time duration on the order of, for example, 120 milliseconds and may be utilized for establishing a baseline for detecting ischemia.

The QRS complex of the ECG then normally occurs after the substantially constant portion with a Q wave which is normally a small negative deflection which is then immediately succeeded by the R wave which is a rapid positive deflection. The R wave generally has an amplitude greater than any other waves of the ECG signal and will have a spiked shape of relatively short duration with a sharp rise, a peak amplitude, and a sharp decline. The R wave may have a duration on the order of 40 milliseconds.

Following the R wave, the QRS complex is completed with an S wave. The S wave may be generally characterized by a small positive inflection in the ECG signal.

Following the S wave is the T wave which is separated from the S wave by the ST segment. The amplitude of the ST segment, in a healthy heart, is generally approximately equal to the baseline following the P wave and preceding the Q wave.

Implantable Subcutaneous Stimulation Device

Figure 3:
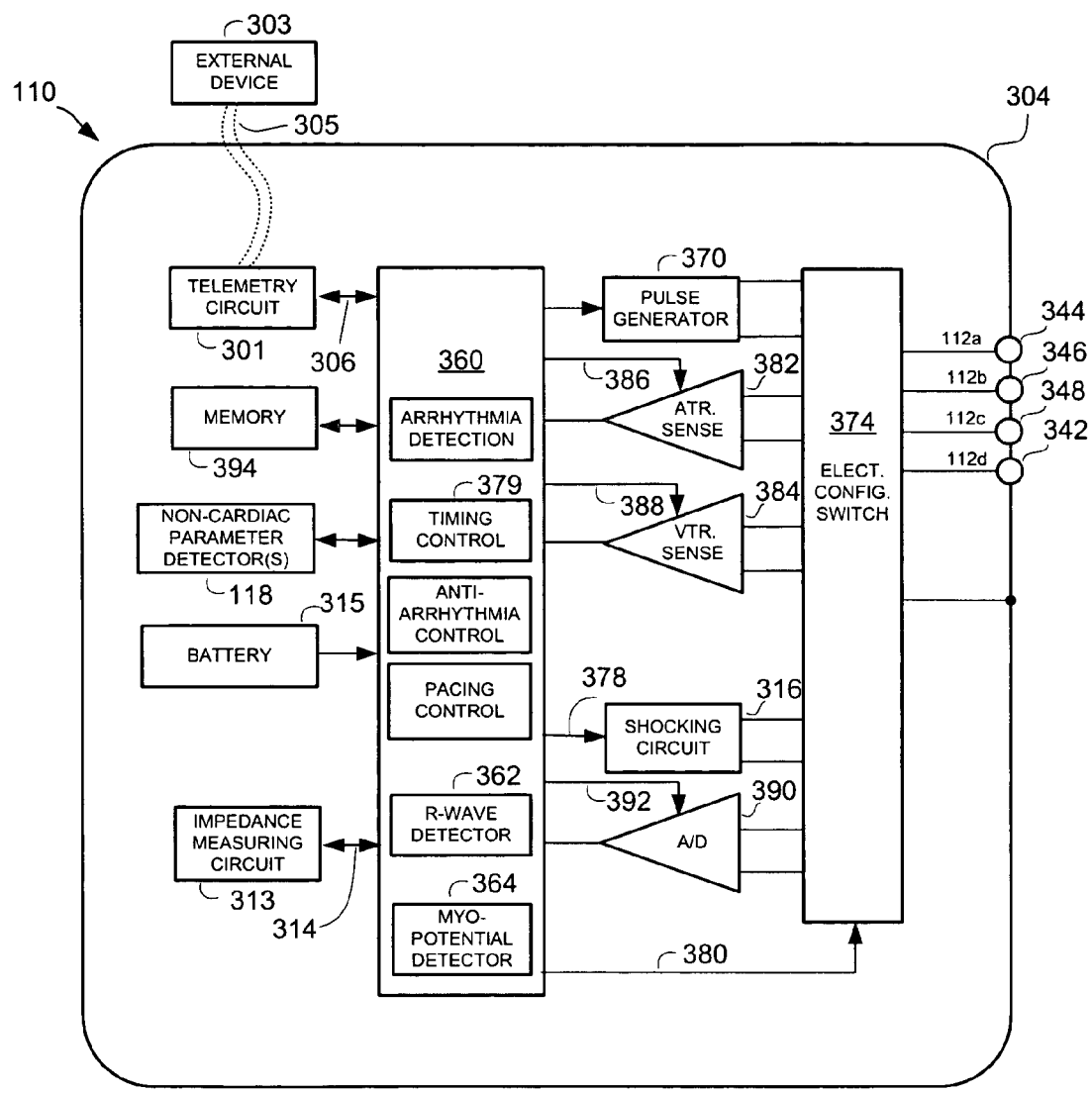
FIG. 3 is a high level diagram of a subcutaneous stimulation device, according to an embodiment of the present invention.

Additional details of a subQ stimulation device 110, according to an embodiment of the present invention, shall now be described with reference to FIG. 3. FIG. 3 is a simplified block diagram of the internal components of the subQ stimulation device 110, which is capable of detecting and treating both fast and slow arrhythmias with stimulation therapy, including cardioversion, defibrillation, and/or pacing stimulation. While particular details are shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

A housing 304 for the stimulation device 110, shown schematically in FIG. 3, (often referred to as the "can", "case" or "case electrode") may be programmably selected to act as the return electrode for all "unipolar" modes. The housing 304 may further be used as a return electrode alone or in combination with one or more electrodes 112 for shocking purposes. The housing 304 further includes a connector (not shown) having a plurality of terminals, 342, 344, 346, 348 etc. (shown schematically and, for convenience, the reference numbers of the extracardiac subQ electrodes 112 to which they are connected are shown next to the terminals).

At the core of the stimulation device 110 is a programmable controller 360 which controls the various modes of stimulation therapy, including anti-arrhythmia therapy. As is well known in the art, the controller 360 typically includes a microprocessor, or equivalent control circuitry, designed specifically for controlling the delivery of stimulation therapy and can further include RAM or ROM memory, logic and timing circuitry, state machine circuitry, and I/O circuitry. Typically, the controller 360 includes the ability to analyze signals (data) as controlled by a program code stored in a designated block of memory. The details of the design of the controller 360 are not critical to the present invention. Rather, any suitable controller 360 can be used to carry out the functions described herein. The use of microprocessor-based control circuits for performing timing and data analysis functions are well known in the art. In specific embodiment of the present invention, the controller 360 performs some or all of the steps associated with monitoring myopotential (including detecting an absence or presence of myopotential, or quantifying levels of myopotential), detecting R-waves, adjusting threshold levels, and the like. Accordingly, the controller is shown as including a myopotential detector block 364 and an R-wave detection block 362.

Exemplary types of control circuitry that may be used with the invention include the microprocessor-based control system of U.S. Pat. No. 4,940,052 (Mann et. al.) and the state-machines of U.S. Pat. No. 4,712,555 (Thornander et al.) and U.S. Pat. No. 4,944,298 (Sholder). For a more detailed description of the various timing intervals used within the stimulation device and their inter-relationship, see U.S. Pat. No. 4,788,980 (Mann et. al.). The '052, '555, '298 and '980 patents are incorporated herein by reference.

As shown in FIG. 3, a pulse generator block 370 generates stimulation pulses for delivery by the subQ extracardiac electrodes 112. It is understood that in order to provide stimulation therapy in more than one chamber of the heart, the pulse generator block 370 may include dedicated, independent pulse generators, multiplexed pulse generators, or shared pulse generators. The pulse generator block 370 is controlled by the controller 360 via appropriate control signals to trigger or inhibit the stimulation pulses.

The controller 360 further includes timing control circuitry 379 which is used to control pacing parameters (e.g., the timing of stimulation pulses) as well as to keep track of the timing of refractory periods, PVARP intervals, noise detection windows, evoked response windows, alert intervals, marker channel timing, etc., which is well known in the art.

A switch bank 374 includes a plurality of switches for connecting the desired subQ extracardiac electrodes 112 to the appropriate I/O circuits, thereby providing complete electrode programmability. Accordingly, the switch bank 374, in response to a control signal 380 from the controller 360, determines the polarity of the stimulation pulses (e.g., unipolar, bipolar, combipolar, etc.) by selectively closing the appropriate combination of switches (not specifically shown) as is known in the art.

Sensing circuits 382 and 384 may also be selectively coupled to the various subQ extracardiac electrodes 112 through the switch bank 374 for detecting the presence of cardiac activity from the heart. Accordingly, the sensing circuits, 382 and 384, may include dedicated sense amplifiers, multiplexed amplifiers, or shared amplifiers. The switch bank 374 determines the "sensing polarity" of the cardiac signal by selectively closing the appropriate switches, as is also known in the art. In this way, the clinician may program the sensing polarity independent of the stimulation polarity.

Each sensing circuit, 382 and 384, preferably employs one or more low power, precision amplifiers with programmable gain and/or automatic gain control, filters. (e.g., for low pass, high pass and/or band pass filtering), and a threshold comparison/detection circuit, as known in the art, to selectively sense the cardiac signal of interest. The automatic gain control enables the device 110 to deal effectively with the difficult problem of sensing the low amplitude signal characteristics of atrial or ventricular fibrillation. Thresholding, match filtering, sliding window correlation, and other types of signal analysis can also be performed within the controller 360.

The outputs of the sensing circuits, 382 and 384, are connected to the controller 360 which, in turn, are able to trigger or inhibit the pulse generator block 370 in a demand fashion in response to the absence or presence of cardiac activity. The sensing circuits, 382 and 384, in turn, receive control signals over signal lines, 386 and 388, from the controller 360 for purposes of measuring cardiac activity at appropriate times, and for controlling the gain, threshold, polarization charge removal circuitry (not shown), and timing of any blocking circuitry (not shown) coupled to the inputs of the sensing circuits, 382 and 386.

For arrhythmia detection, the device 110 utilizes the sensing circuits, 382 and 384, to sense cardiac signals to determine whether a rhythm is physiologic or pathologic. The timing intervals between sensed events (e.g., P-waves, R-waves, and depolarization signals associated with fibrillation which are sometimes referred to as "F-waves" or "Fib-waves") are then classified by the controller 360, e.g., by comparing them to predefined of self calibrating (i.e., updating) rate zone limits (e.g., bradycardia, normal, low rate VT, high rate VT, and fibrillation rate zones) and various other characteristics (e.g., sudden onset, stability, physiologic sensors, and morphology, etc.) in order to assist with determining the type of remedial therapy that is needed (e.g., bradycardia pacing, anti-tachycardia pacing, cardioversion shocks or defibrillation shocks, collectively referred to as "tiered therapy"). Specific schemes for detecting VT and VF are discussed below with reference to FIGS. 14A-14E.

Cardiac signals are also applied to the inputs of an analog-to-digital (A/D) data acquisition system 390. The data acquisition system 390 is configured to acquire intracardiac electrogram signals, convert the raw analog data into a digital signal, and store the digital signals for later processing and/or telemetric transmission to an external device 303. The data acquisition system 390 is coupled to subQ extracardiac electrodes 112 through the switch bank 374 to sample cardiac signals across any pair of desired electrodes.

Advantageously, the data acquisition system 390 can be coupled to the controller 360, or other detection circuitry, for detecting an evoked response from the heart in response to an applied stimulus, thereby aiding in the detection of "capture". Capture occurs when an electrical stimulus applied to the heart is of sufficient energy to depolarize the cardiac tissue, thereby causing the heart muscle to contract. The controller 360 detects a depolarization signal during a window following a stimulation pulse, the presence of which indicates that capture has occurred. The controller 360 enables capture detection by triggering the pulse generator 370 to generate a stimulation pulse, starting a capture detection window using the timing control circuitry 379 within the controller 360, and enabling the data acquisition system 390 via control signal 392 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et al.); and U.S. Pat. No. 5,350,410 (Kleks et al.), which patents are hereby incorporated herein by reference. The type of capture detection system used is not critical to the present invention.

The controller 360 is further coupled to a memory 394 by a suitable data/address bus, wherein the programmable operating parameters used by the controller 360 are stored and modified, as required, in order to customize the operation of the stimulation device 110 to suit the needs of a particular patient. Such operating parameters define, for example, pacing pulse amplitude, pulse duration, electrode polarity, rate, sensitivity, automatic features, arrhythmia detection criteria, initial R-wave detection parameters, and the amplitude, waveshape and vector of each shocking pulse to be delivered to the patient's heart within each respective tier of therapy. The memory 394, or a further memory, can also be used to store hemodynamic and/or physiologic data that is obtained by the device 110.

Advantageously, the operating parameters of the implantable device 110 may be non-invasively programmed into the memory 394 through a telemetry circuit 301 in telemetric communication with an external device 303, such as a programmer, transtelephonic transceiver, or a diagnostic system analyzer. The telemetry circuit 301 is activated by the controller 360 by a control signal 306. The telemetry circuit 301 advantageously allows intracardiac electrograms and status information relating to the operation of the device 110 (as contained in the controller 360 or memory 394) to be sent to the external device 303 through an established communication link 305.

Examples of telemetry circuits are described in the following U.S. patents, each of which is incorporated herein by reference: U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734, entitled "Efficient Generation of Sensing Signals in an Implantable Medical Device such as a Pacemaker or ICD" (McClure et al.). Another example of a telemetric circuit for use in a chronically implantable device is the TR1000 transceiver manufactured by RF Monolithics, Dallas, Tex. The TR 1000 is a single-chip, low-power, 916.5 MHz transceiver. An operating frequency of about 916.5 MHz is typically desirable because of the modest requirements on antenna size it imposes. Such telemetry circuits can use, e.g., magnetic induction, radio telemetry or acoustic telemetry.

In accordance with an embodiment, the stimulation device 110 further includes one or more extracadiac parameter detector 118, which as mentioned above, can be located within the stimulation device housing 304 as shown in FIG. 3, or can be located external to the housing as shown in FIG. 1.

A battery 315 provides operating power to all of the circuits shown in FIG. 3. If the stimulation device 110 employs shocking therapy, the battery 315 should be capable of operating at low current drains for long periods of time, and then be capable of providing high-current pulses (for capacitor charging) when the patient requires a shock pulse. The battery 315 should also have a predictable discharge characteristic so that elective replacement time can be detected. Accordingly, the device 110 preferably employs lithium/silver vanadium oxide batteries, as is true for most (if not all) current devices, but is not limited thereto.

The stimulation device 110 can also include a magnet detection circuitry (not shown), coupled to the controller 360. It is the purpose of the magnet detection circuitry to detect when a magnet is placed over the stimulation device 110. The magnet may be used by a clinician to perform various test functions of the stimulation device 110 and/or to signal the controller 360 that the external programmer 303 is in place to receive or transmit data to the controller 360 through the telemetry circuits 301.

As further shown in FIG. 3, the device 110 is shown as having an impedance measuring circuit 313 which is enabled by the controller 360 via a control signal 314. The known uses for an impedance measuring circuit 313 include, but are not limited to, lead impedance surveillance during the acute and chronic phases for proper lead positioning or dislodgement;

detecting operable electrodes and automatically switching to an operable pair if dislodgement occurs; measuring respiration or minute ventilation; measuring thoracic impedance for determining shock thresholds; measuring thoracic impedance for detecting and assessing the severity of pulmonary edema; detecting when the device has been implanted; measuring stroke volume; and detecting the opening of heart valves, etc. The impedance measuring circuit 313 is advantageously coupled to the switch bank 374 so that any desired electrode may be used. In addition, to facilitate the measurement of peripheral tissue edema, extra electrodes can be added to the device housing, thereby limiting the test electric field to the peripheral tissue.

In the case where the stimulation device 110 is intended to operate as an implantable cardioverter defibrillator (ICD) device, it must detect the occurrence of an arrhythmia, and automatically apply an appropriate electrical shock therapy to the heart aimed at terminating the detected arrhythmia. To this end, the controller 360 further controls a shocking circuit 316 by way of a control signal 378. The shocking circuit 316 generates shocking pulses of low (up to 0.5 Joules), moderate (0.5-10 Joules), or high energy (11 to 40 Joules), as controlled by the controller 360. Such shocking pulses are applied to the patient's heart through at least two electrodes. As noted above, the housing 304 may act as an active electrode in combination with one of the subQ extracardiac electrodes 112.

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 Joules), delivered asynchronously (since R-waves may be too disorganized to be recognized), and pertaining exclusively to the treatment of fibrillation. Accordingly, the controller 360 is capable of controlling the synchronous or asynchronous delivery of the shocking pulses. Another approach to electrical anti-arrhythmia therapy is anti-tachycardia pacing, in which low-voltage pacing pulses are applied to pace-terminate the arrhythmia. This approach is particularly effective in low rate ventricular tachycardias.

Additional and alternative details of implantable cardiac stimulation devices can be found in U.S. Pat. No. 5,405,363 (Kroll et al.) and U.S. Pat. No. 5,040,534 (Mann et al.), both of which are incorporated herein by reference.

Now that an exemplary cardiac stimulation device has been described, further embodiments of the present invention will be described in more detail.

R-Wave Detection

Figure 4:
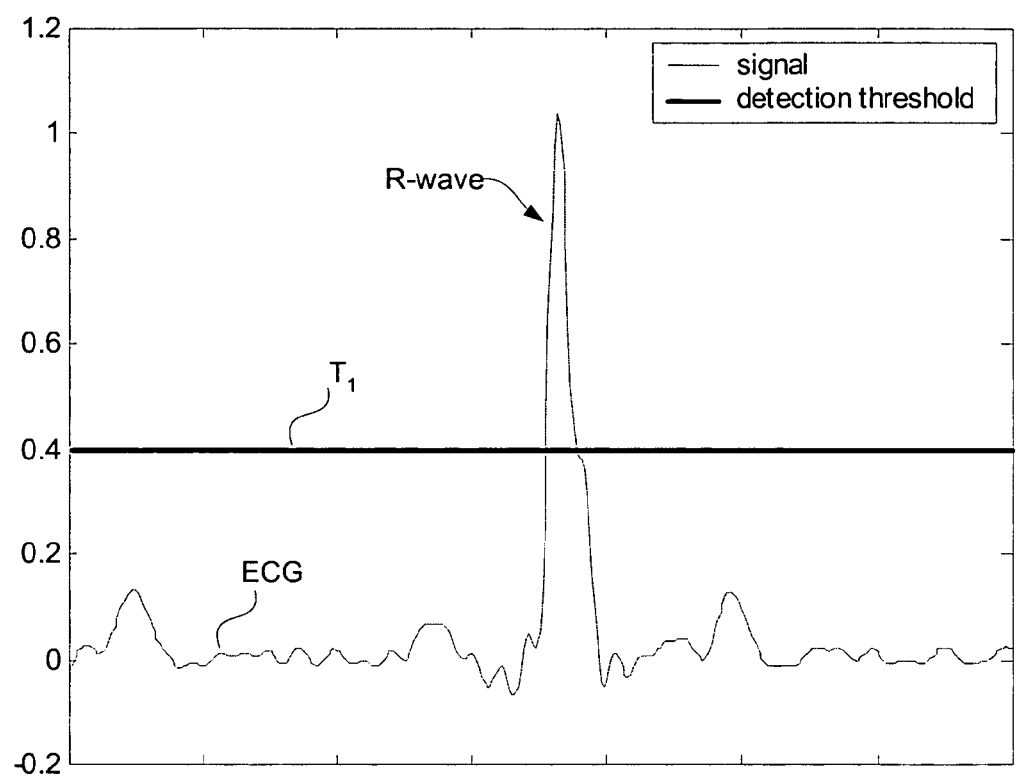
FIG. 4 illustrates a graph that is useful for describing a simple conventional R-wave detection scheme that uses a constant R-wave detection threshold.

Some embodiments of the present invention are directed to systems and methods for detecting R-waves, as well as for adjusting thresholds that are used to detect R-waves. The graph of FIG. 4 is used to describe a simple conventional R-wave detection scheme in which an R-wave detection occurs whenever the ECG waveform exceeds a constant detection threshold $T_1$ (e.g., 0.4 mV). However, the mean amplitudes of ECG signals sensed (i.e., detected) using extracardiac subQ electrodes (e.g., 112) can tend to change over time, e.g., due to movement of the electrodes, intermittent contact problems, tissue growth over the electrodes, changes in breathing, etc. Such sensing issues are particularly problematic when the sensing electrodes are far and spatially removed from the heart, such as in the case of extracardiac subQ electrodes. Accordingly, the following embodiments of the present invention are used to adapt to changes in ECG signal trends. More specifically, these embodiments adaptively change the R-wave detection threshold.

Figure 5:
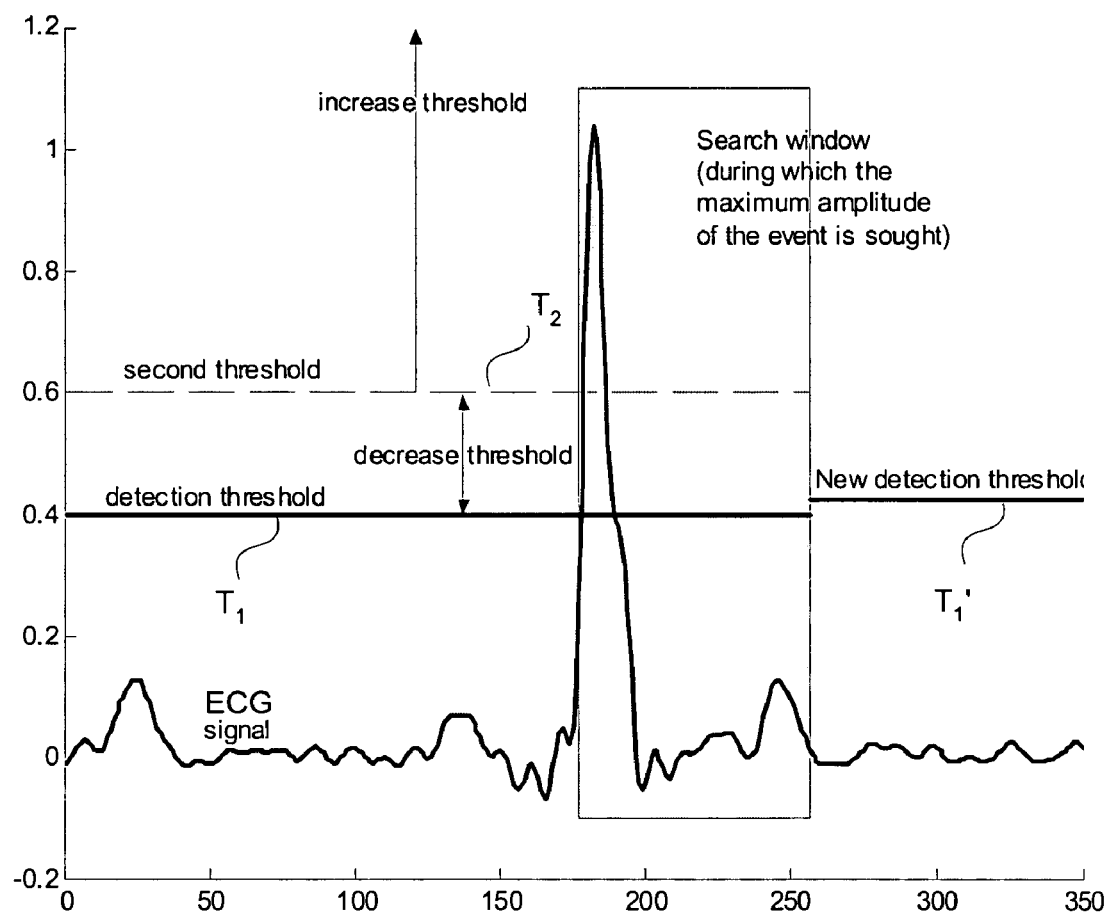
FIG. 5 illustrates a graph that is useful for describing a scheme for adjusting an R-wave detection threshold in accordance with an embodiment of the present invention.

The graph of FIG. 5 is used to describe a first scheme of the present invention for detecting R-waves. These features, as well as the features of the further embodiments described with reference to FIGS. 5-8, can be performed, e.g., by the R-wave detector 362 shown in FIG. 3. In this embodiment, there is a first threshold $T_1$, also referred to as the adjustable R-wave detection threshold and a higher second threshold $T_2$, which is used to quantify the amplitude of the cardiac event represented by the ECG waveform. The second threshold $T_2$ can be set as a predetermined value (e.g., 0.2V) or a predetermined percentage (e.g., 50%) greater than the present detection threshold $T_1$. In the graph of FIG. 5, the detection threshold $T_1$ is initially shown as being equal to 0.4 mV, and the second threshold $T_2$ is shown as being equal to 0.6 mV (e.g., $T_2=T_1+0.2$ mV; or $T_2=T_1+(0.5*T_1)$). In accordance with this embodiment, during a window (of fixed or non-fixed width) following an R-wave detection, there is a determination of whether the second threshold $T_2$ is exceeded. If the second threshold $T_2$ is exceeded, as shown in FIG. 5, then the detection threshold $T_1$ is increased (e.g., by a predefined value or percentage) to define an updated detection threshold $T_1'$. If the second threshold $T_2$ is not exceeded, then the detection threshold $T_1$ is decreased, e.g., by another (or the same) predefined value or percentage. The amount of the increase and the amount of the decrease used determines how fast the detection threshold $T_1$ adapts to signal trends.

Figure 6:
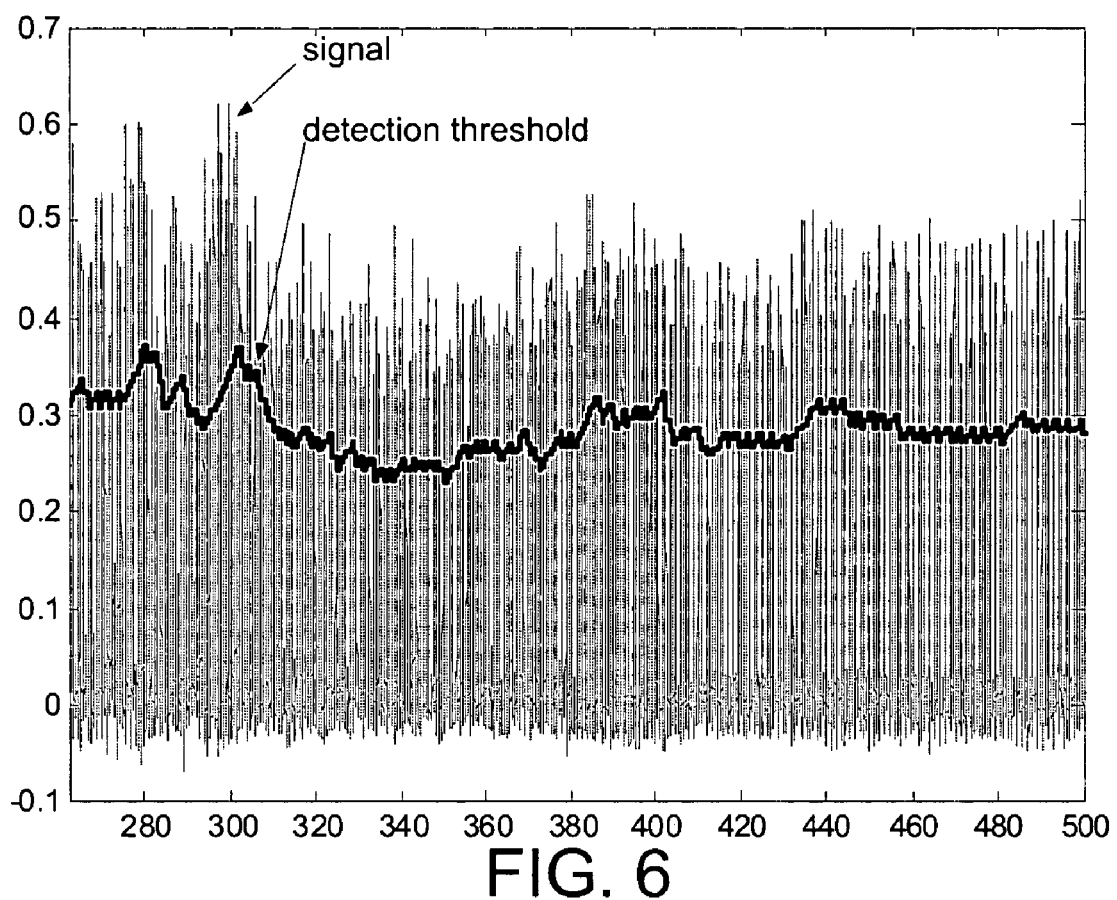
FIG. 6 illustrates a graph that shows how the detection threshold is adjusted using a specific implementation of the scheme described with reference to FIG. 5.

FIG. 6 shows how this embodiment of the present invention performs in a specific case where: the detection threshold $T_1$ is increased by 2.1% when the second threshold $T_2$ is exceeded; the detection threshold is decreased by 4.2% when the second threshold $T_2$ is not exceeded; and where the second threshold $T_2$ is set to be 43% higher than the detection threshold $T_1$, giving a safety margin of approximately 30%.

Figure 7:
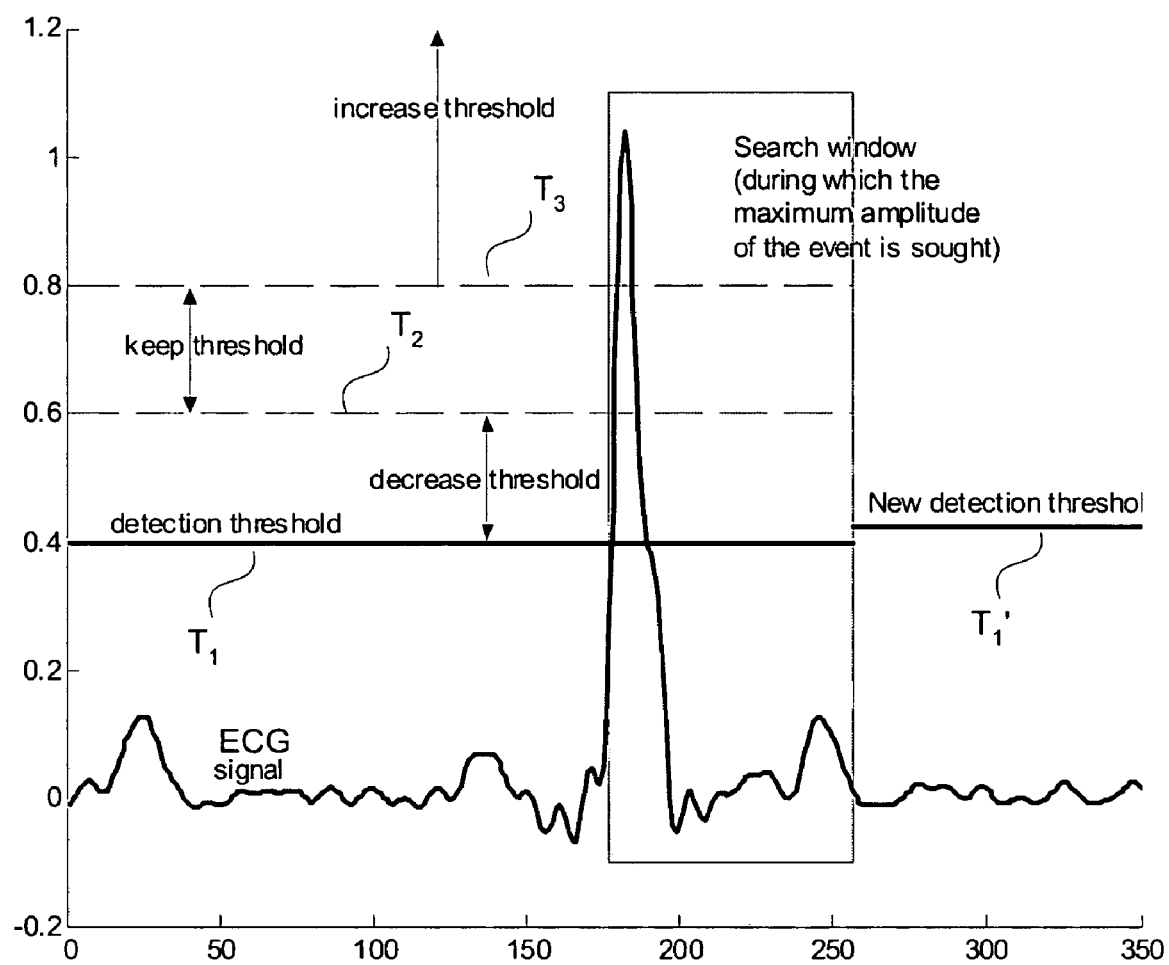
FIG. 7 illustrates a graph that is useful for describing a scheme for adjusting an R-wave detection threshold in accordance with another embodiment of the present invention.

The graph of FIG. 7 is used to describe another embodiment for detecting R-waves. In this embodiment, there is a first threshold $T_1$, also referred to as the adjustable detection threshold, a higher second threshold $T_2$, and an even higher third threshold $T_3$, with the second and third thresholds being used to quantify the amplitude of the cardiac event represented by the ECG waveform. In the graph of FIG. 5, the detection threshold $T_1$ is initially shown as being equal to 0.4 mV, the second threshold $T_2$ is shown as being equal to 0.6 mV (e.g., $T_2=T_1+0.2$ mV; or $T_2=T_1+(0.5*T_1)$) and the third threshold $T_3$ is shown as being equal to 0.8 mV (e.g., $T_3=T_1+0.4$ mV; or $T_2=2*T_1$). In accordance with this embodiment, during a window following an R-wave detection, there is a determination of whether the second threshold $T_2$ and the third threshold $T_3$ are exceeded. If the second threshold $T_2$ and the third threshold $T_3$ are both exceeded, as shown in FIG. 7, then the detection threshold $T_1$ is increased, e.g., by a predefined value or percentage, to define an updated detection threshold $T_1'$. If the second threshold $T_2$ is not exceeded, then the detection threshold $T_1$ is decreased, e.g., by another (or the same) predefined value or percentage. If the second threshold $T_2$ is exceeded, but the third threshold $T_3$ is not exceeded, then the first threshold is kept the same. The amount of the increase and the amount of the decrease used determines how fast the detection threshold $T_1$ adapts to signal trends.

Figure 8:
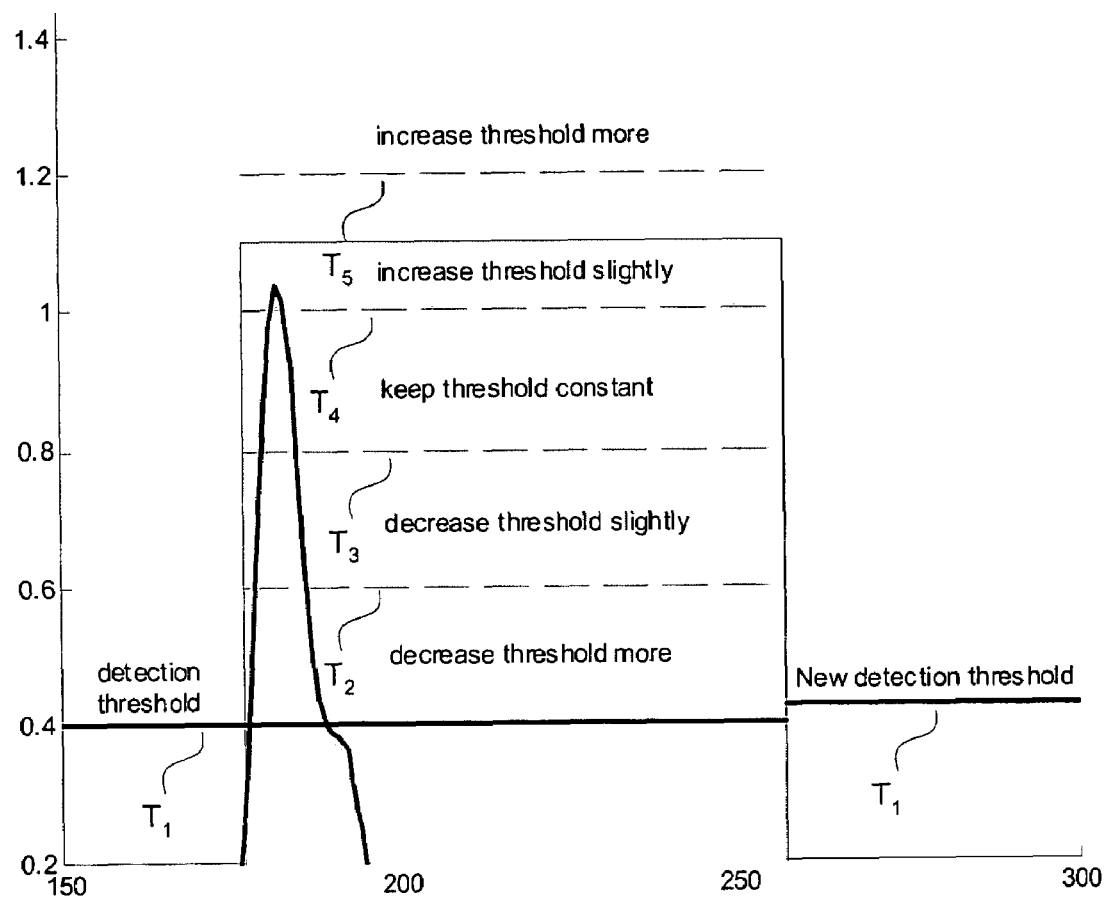
FIG. 8 illustrates a graph that is useful for describing a scheme for adjusting an R-wave detection threshold in accordance with still a further embodiment of the present invention.

A further expansion of the embodiments discussed above is to use additional thresholds to divide the region above the detection threshold $T_1$ into even more parts, and to differently change the detection threshold $T_1$ depending on which amplitude(s) are exceeded. For example, as shown in FIG. 8, there can be a detection threshold $T_1$ and four additional thresholds $T_2, T_3, T_4$ and $T_5$. In accordance with such an embodiment, if the second threshold $T_2$ is not exceeded, then the detection threshold $T_1$ would be decreased by an amount (e.g., a value or percentage). If the second threshold $T_2$ is exceeded, but the third threshold $T_3$ is not exceeded, then the detection threshold $T_1$ would be decreased by a lesser amount (e.g., a lesser value or percentage). If the third threshold $T_3$ is exceeded, but the fourth threshold $T_4$ is not, then the detection threshold $T_1$ would be kept constant. If the fourth threshold $T_4$ is exceeded, but the fifth threshold $T_5$ is not exceeded, then the detection threshold $T_1$ would be increased by an amount (e.g., a value or percentage). If the fifth threshold $T_5$ is exceeded, then the detection threshold $T_1$ would be increased by a greater amount (e.g., a greater value or percentage).

In still another embodiment of the present invention, the region above the detection threshold is divided into an infinite number or regions. More specifically, the change in the detection threshold is set as a linear function of the maximum amplitude during a window of time (of fixed or non-fixed width) following an R-wave detection, using the formula: Δdetection threshold=k*(max amplitude−second threshold), where k is a scaling factor that can be set to any positive number, and the second threshold defines the point at which the detection threshold is either increased, kept constant, or decreased (i.e., if the maximum amplitude is greater than the second threshold, then Δ detection threshold will be a positive amount; if the maximum amplitude is equal to the second threshold, then Δ detection threshold will be zero; and if the maximum amplitude is less than the second threshold, then Δ detection threshold will be a negative amount). The second threshold is preferably a function of the detection threshold, e.g., a percentage of the detection threshold, or the detection threshold plus a constant. For example, if the second threshold=1.5*detection threshold, then the safety margin will be approximately 1−(1/1.5)=0.33=33%.

By using the above described embodiments for adjusting the R-wave detection threshold, the region where the detection threshold becomes relatively stable is driven to the mean amplitude of the detections. Thus, the second threshold or whatever specifies the signal amplitude at which the detection threshold is unchanged is tightly linked to the safety margin of the system.

Myopotential Detection

Proper detection of ventricular signals depends heavily on the amount of "noise" present in the signal. In accordance with embodiments of the present invention, it is assumed that the primary sources of noise in ventricular signals arise from skeletal myopotentials (i.e., electrical signals originating from skeletal muscles) and motion artifacts. The flow diagram in FIG. 9 will be used to describe myopotential detection (e.g., as performed by a myopotential detector), in accordance with embodiments of the present invention.

In accordance with embodiments of the present invention, a myopotential detector (e.g., 364 in FIG. 3) continuously assesses the level of myopotential activity in a signal by applying a histogram to a rectified high pass filtered (e.g., at 40 Hz) output of the present signal. The variation in distribution of the present signal's amplitudes relative to the distribution of the signal amplitudes at rest (i.e., when the least amount of noise is present) is constantly monitored. For example, in one embodiment, the ratio between the number of points in a highest N bins vs. the number of points in the lowest M bins of a histogram, where M and N are positive integer values and M+N≦Total number of bins, can be used to track changes. In another embodiment, the slope of a best linear fit line to the histogram distribution can be used to track changes. The myopotential detector then uses two (predefined or programmable) threshold values (e.g., ratio threshold values or slope threshold values) to assign a low (Lo), a medium (Mid), or a high (Hi) classification to the "noise," to indicate the level of myopotential present in the signal over the window (in time) that it processed. The length of the window can be, e.g., anywhere between a few hundred milliseconds to a few seconds, but is not limited thereto.

For the following description, a sensing vector can be thought of as the spatial area between a positive electrode and a negative electrode. Embodiments of the present invention can be used to detect the level of myopotential activity for a single sensing vector, or multiple sensing vectors. For example, for a first sensing vector, the positive electrode can be a subQ electrode 112 near the bottom of the sternum, and the negative electrode can be a subQ electrode 112 below the left pectoral area, below the clavicle. For a second sensing vector, the positive electrode can be the subQ electrode 112 near the bottom of the sternum, and the negative electrode can be a subQ electrode 112 on the back left side, just below the shoulder blade. These are just two examples of many possible sensing vectors. As just shown, different sensing vectors can share a common electrode, but need not. Uses of other sensing vectors are within the scope of the present invention. Preferably, the signal for each sensing vector is zero mean rectified and high pass filtered (e.g., using a cutoff frequency of about 40 Hz) before the maximum and minimum amplitudes are determined. Rather than zero mean rectifying, other ways to get the signals (or the samples produced therefrom) to have a common polarity can be used, such as squaring or determining absolute values. Also, band pass filtering can be used instead of high pass filtering, as one of ordinary skill in the art would understand.

If the myopotential activity is being assessed for multiple sensing vectors, then preferably, the sensing vectors should be selected such that the same myopotential detected by one of the vectors will not be detected by the other one of the vectors. This can be accomplished by arranging the vectors spatially far enough from one another so that they cover different muscle groups, which are unlikely to be highly active at the same time.

Figure 9:
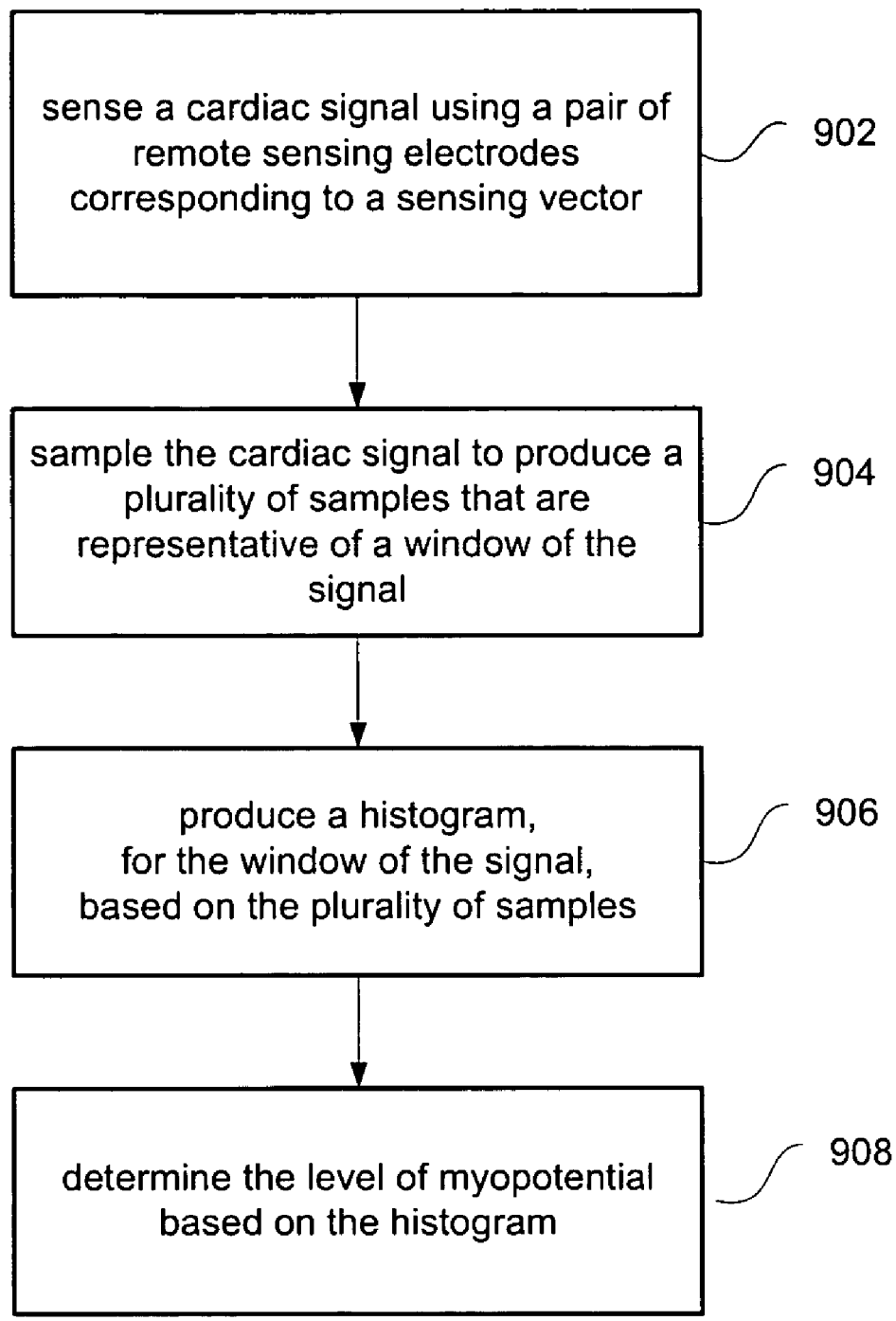
FIG. 9 is a high level flow diagram that is useful for describing systems and methods for myopotential detection, in accordance with embodiments of the present invention.

Referring to FIG. 9, at a step 902, a cardiac signal (e.g., an ECG signal) is sensed using a pair of remote sensing electrodes (e.g., subQ extracardiac electrodes 112) corresponding to a sensing vector.

At a step 904, the cardiac signal is sampled to produce a plurality of samples (e.g., 1000 samples) that are representative of the window of the cardiac signal.

Next, myopotential is detected based on the plurality of samples. This may include determining a level of myopotential level on the plurality of samples. In accordance with specific embodiments of the present invention, this is accomplished by producing a histogram, based on the plurality of samples, at step 906. Then, at step 908, the level of myopotential is determined based on the histogram.

Figure 10A:
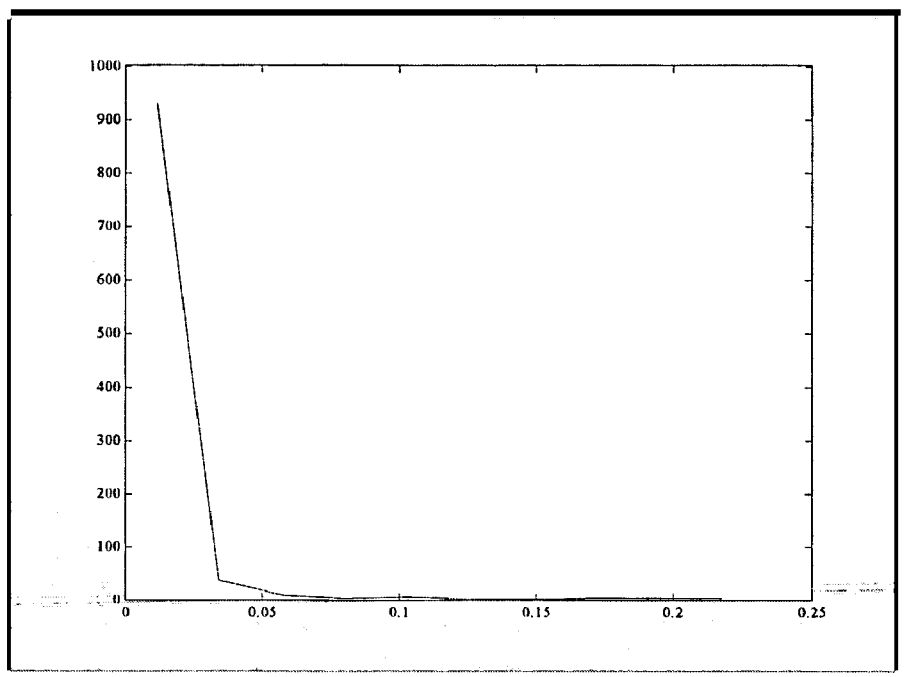
FIGS. 10A and 10B are exemplary histograms that can be used for myopotential detection, in accordance with embodiments of the present invention.

A first exemplary histogram is shown in FIG. 10A, with the horizontal axis showing bins, and the vertical axis showing number of samples per bin. Five bins are shown, with the first bin being from 0 to 0.05 millivolts (mV), the second bin being from 0.05 to 0.10 mV, the third bin being from 0.10 to 0.15 mV, the fourth bin being from 0.15 volts to 0.20 mV, and the fifth bin being from 0.20 volts to 0.25 mV. The histogram of FIG. 10A was produced while a patient was at rest with normal sinus condition, as can be appreciated from the fact that over 900 of the samples are in the first (i.e., lowest voltage) bin, while hardly any samples are in the last (i.e., highest voltage) bin.

Figure 10B:
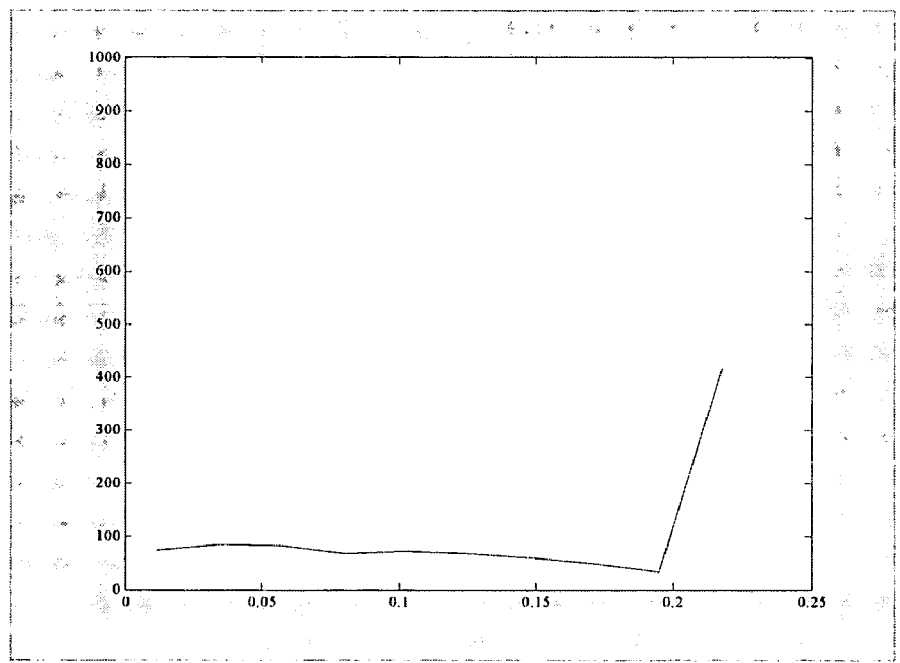

A second exemplary histogram is shown in FIG. 10B. The histogram of FIG. 10B was produced while the patient was performing chest presses, and thus, a high level myopotential was present. As can be seen from FIG. 10B, less than 100 samples are within each of the first four bins, but over 400 samples are in the last (i.e., highest voltage) bin.

As mentioned above, at a step 908, the level of myopotential in a signal is determined based on the histogram. In accordance with specific embodiments of the present invention, the level of myopotential is determined based on a ratio of the number of samples in the last (i.e., highest voltage) bin to the number of samples in the first (i.e., lowest voltage) bin, or vice versa. A single threshold (predefined or programmable) can be used to detect an absence or presence of myopotential, or in a specific embodiment, to assign a low (Lo) or high (Hi) level of myopotential level to the signal. In accordance with other embodiments, two or more thresholds can be used to assign three or more levels of myopotential level. In a specific embodiment, two (predefined or programmable) threshold values are used to assign a low (Lo), a medium (Mid), or a high (Hi) classification to the level of myopotential present in the signal over the window (in time). For example, the actual ratio of the number of samples in the highest bin to the number of samples in the lowest bin can be compared to a low ratio threshold and a high ratio threshold. If the actual ratio is less than the low ratio threshold, then it is determined that the myopotential level is low. If the actual ratio is between the low and high ratio thresholds, then it is determined that the myopotential level is medium. If the actual ratio is greater than the high ratio threshold, then it is determined that the myopotential level is high.

In other embodiments, a slope of a best linear fit line to the distribution can be determined. Then the slope can be compared to one or more slope thresholds, in a similar manner as described above, to monitor myopotential, or more specifically, to classify the level of myopotential.

Embodiments of the present invention are also directed to monitoring whether myopotential is present or absent in a sensing channel. This can be accomplished, e.g., using a myopotential detection threshold. For example, if a histogram ratio (or a slope of a line fit to the histogram distribution) is less than the detection threshold, it can be concluded that myopotential is absent. On the other hand, if the threshold is exceeded, it can be concluded that myopotential is present. Additional thresholds can also be used to quantify the level of the myopotential that is present, in the manners described above.

As is apparent from the above description, more thresholds can be used to classify the level of myopotential present in a signal into as many levels as desired.

Activity/Posture Detection

An activity and/or posture detector can analyzes the output of an accelerometer or other sensor to detect presence of high impact activity and possibly motion artifacts. When a 3 D accelerometer is available, posture information can also be extracted. The following patents, which above were incorporated herein by reference, describe exemplary activity sensors that can be used to detect activity of a patient (some also detect posture): U.S. Pat. No. 6,658,292 to Kroll et al., entitled "Detection of Patient's Position and Activity Status using 3 D Accelerometer-Based Position Sensor"; U.S. Pat. No. 6,625,493 to Kroll et al., entitled "Orientation of Patient's Position Sensor using External Field"; and U.S. Pat. No. 6,466,821 to Pianca et al., entitled "AC/DC Multi-Axis Accelerometer for Determining Patient Activity and Body Position."

When an activity detector indicates presence of high impact activity, it can be assumed that motion artifacts are present in the signal which can interfere with proper R-wave detection. This can trigger a Motion-Artifact-Remover (MAR) unit to turn ON.

When enabled, this MAR can simply apply a high pass filter (e.g. with cut off at around 4-5 Hz) to the signal. Alternatively, it can apply a specialized filter such as a "max-min" filter to the signal. The "max-min" filter is essentially a high-pass non-linear filter that is very easy to implement. This filter replaces every sample in the signal by the difference in the lowest and highest amplitude samples in a small window of length Q into the past (e.g. Q can be equal to the last 100 ms prior to the present sample). In other words, every sample i in the signal x (i.e., $x_i$) is replaced by $y_i$ where:

$$y_i = \max\{x_{i-Q}, \ldots, x_i\} - \min\{x_{i-Q}, \ldots, x_i\}.$$

When enabled, the MAR reduces/removes not only the low-frequency motion artifacts, but also monomorphic/polymorphic VT's and VF's. As such, motion artifact removal is preferably only used during "low" myopotential levels. This ensures that during "mid" myopotential levels, where R-wave detection may be dependent on the signal morphology (e.g., using match filtering), signal morphology remains intact.

It should be noted that the "max-min" filter can be applied to any application where removal of low frequency signal components is desired and its application should not be limited to what is discussed in this disclosure.

Presence of pronounced T-waves in the signal, which may be very similar to motion artifacts in appearance, can pose a more challenging problem (since there is no detector for presence of large T-waves to enable a removal technique as is for motion). As such, T-wave removal by a high pass non-linear filter such as the "max-min" filter can be adopted continuously during "low" myopotential levels. This procedure is preferably not used during "mid" myopotential levels for reasons related to signal morphology discussed above.

Self Tuning of Myopotential Detection Factors

Figure 11:
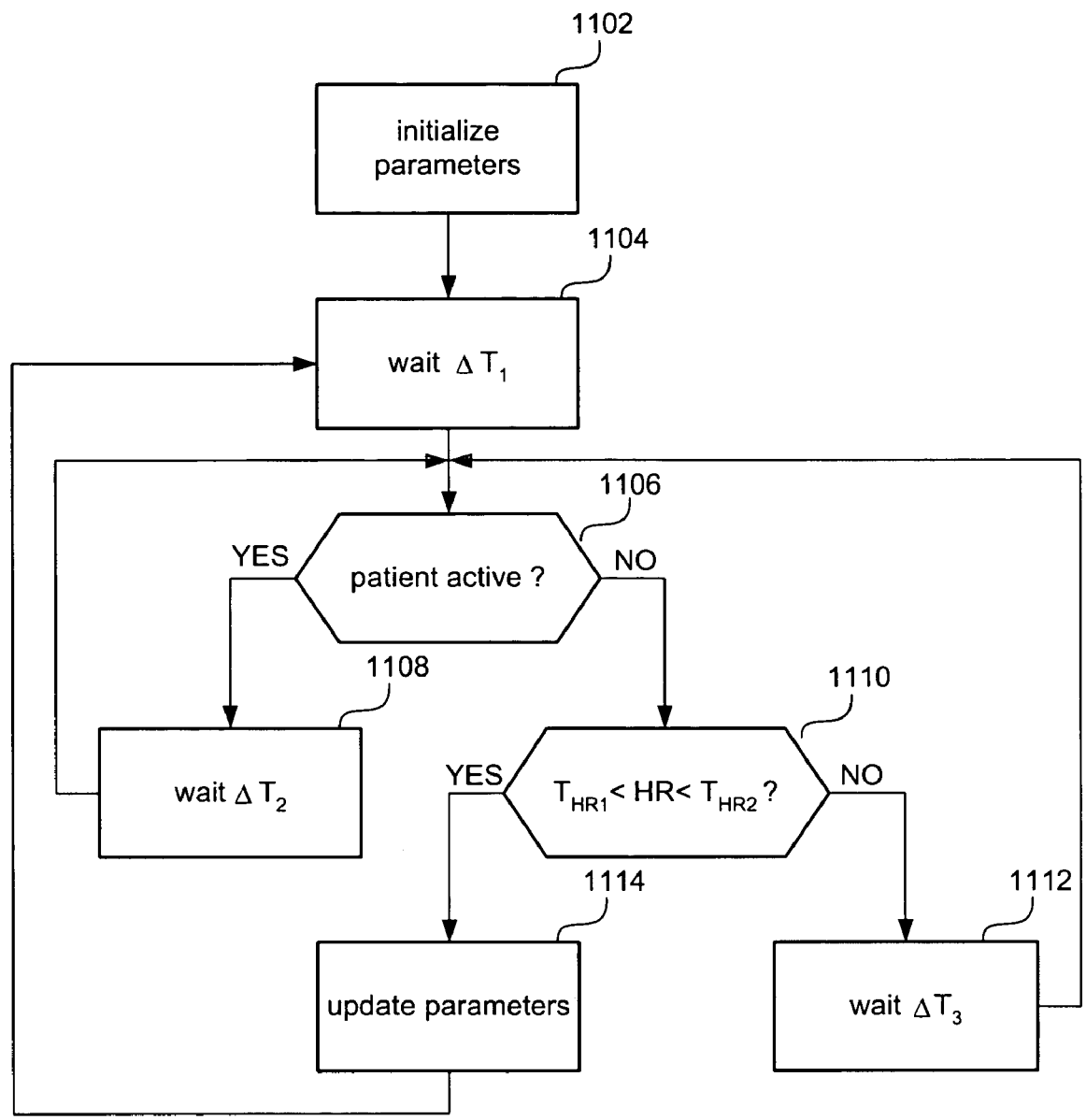
FIG. 11 is a high level flow diagram that is useful for describing how parameters used for myopotential detection can be updated in accordance with an embodiment of the present invention.

The high level flow diagram of FIG. 11 will now be used to describe embodiments of the present invention where the parameters that are used to classify a signal's myopotential level are initially programmed, and then updated over time (e.g., periodically). As described above, such parameters can be ratio thresholds, slope thresholds, as well as highest and lowest bin edges.

Referring to FIG. 11, at a step 1102 the parameters are initially programmed. For example, the initial parameters can be predefined or selected based on results of tests. More specifically, the initial parameters could be pre-programmed into the device 110, or selected by a physician in response to tests performed under the supervision of the physician. For example, the patient can be asked to perform a series of simple exercises that will enable the physician to set parameter values such that muscle activity can be accurately determined. Alternatively, a formula could be used to derive initial parameter values, e.g., based on measured R-wave amplitudes.

After the parameters are initialized, a programmable time period ($\Delta T_1$) is waited, as indicated at step 1104. Such a programmable time period ($\Delta T_1$) is likely to be on the order of hours or days, but is not limited thereto. This step can be accomplished by checking whether an amount of time equal to or greater than $\Delta T_1$ has passed. If it has, flow goes to step 1106.

At step 1106, there is a determination of whether the patient is presently active. This determination can be performed using an activity sensor, such as an accelerometer or similar sensor. Exemplary activity sensors are described in the following patents, each of which was incorporated by reference above: U.S. Pat. No. 6,658,292 (Kroll et al.) describes use of a DC-coupled 3-dimensional accelerometer; U.S. Pat. No. 6,625,493 (Kroll et al.) describes use of a multi-axis DC accelerometer; and U.S. Pat. No. 6,466,821 (Pianca et al.) describes use of an external field sensor. As mentioned above in the discussion of FIGS. 1 and 3, an activity sensor is one example of a non-cardiac parameter detector 118.

If it is determined at step 1106 that the patient is presently active, flow goes to step 1108. At step 1108 a programmable time period ($\Delta T_2$) is waited, before flow returns to step 1106 where there is another determination of the activity of the patient.

When there is a determination at step 1106 that the patient is not active, then flow goes to step 1110, where there is a determination of whether the patient's heart rate (HR) is within an acceptable range, i.e., between a first HR threshold $T_{HR1}$ and a second HR threshold $T_{HR2}$. If the patent's heart rate is not within the acceptable range, a programmable time period ($\Delta T_3$) is waited at step 1112, before flow returns to step 1106 where there is another determination of the activity of the patient. The various programmable time periods can be the same, or they may differ from one another. In accordance with a specific embodiment, $\Delta T_1 > \Delta T_2 = \Delta T_3$, however other variations are within the spirit and scope of the present invention.

When there is a determination at step 1106 that the patient is not active, and there is a determination at step 1110 that the patient's heart rate is within the acceptable range, then flow goes to step 1114, where the myopotential detection parameters are updated. Parameters can be updated in various different manners, some of which are described below.

In accordance with some embodiments of the present invention, the low and high thresholds, $T_L$ and $T_H$, are updated as a function of the change in R-wave amplitudes or R-wave detection thresholds. Such low and high thresholds can be, e.g., ratio thresholds or slope thresholds, as explained above. These embodiments can include, if the R-wave amplitude or R-wave detection threshold has increased, then increasing $T_L$ and $T_H$ by a fixed scaling factor, or by a scaling factor that is a function of the amount of change (i.e., increase) in the R-wave amplitude or detection threshold. For example, updated $T_L$=old $T_L$*1.1, and updated $T_H$=old $T_H$*1.1; or the updated $T_L$=old $T_L$*(1+$\Delta$R), and the updated $T_H$=old $T_H$*(1+$\Delta$R). Similarly, if the R-wave amplitude or R-wave detection threshold has decreased, then $T_L$ and $T_H$ can be decreased by a fixed scaling factor, or by a scaling factor that is a function of the amount of change (i.e., decrease) in the R-wave amplitude or detection threshold. For example, updated $T_L$=old $T_L$*0.9, and updated $T_H$=old $T_H$*0.9; or the updated $T_L$=old $T_L$*(1-$\Delta$R), and the updated $T_H$=old $T_H$*(1-$\Delta$R). These are just a few examples of how threshold parameters (e.g., $T_L$ and $T_H$) can be updated at step 1114. Other schemes are within the spirit and scope of the present invention.

In accordance with other embodiments, the low threshold $T_L$ can be updated using the equation: updated $T_L$=$F_L$*$N_L$/$N_H$, where $F_L$ is a scaling factor used to adjust the low threshold $T_L$, $N_L$ is the number of samples in the lowest bin, and $N_H$ is the number of sample in the highest bin. Similarly, the high threshold $T_H$ can be updated using the equation: updated $T_H$=$F_H$*$N_L$/$N_H$, where $F_H$ is a scaling factor used to adjust a high threshold $T_H$, $N_L$ is the number of samples in the lowest bin, and $N_H$ is the number of sample in the highest bin.

Figure 13:
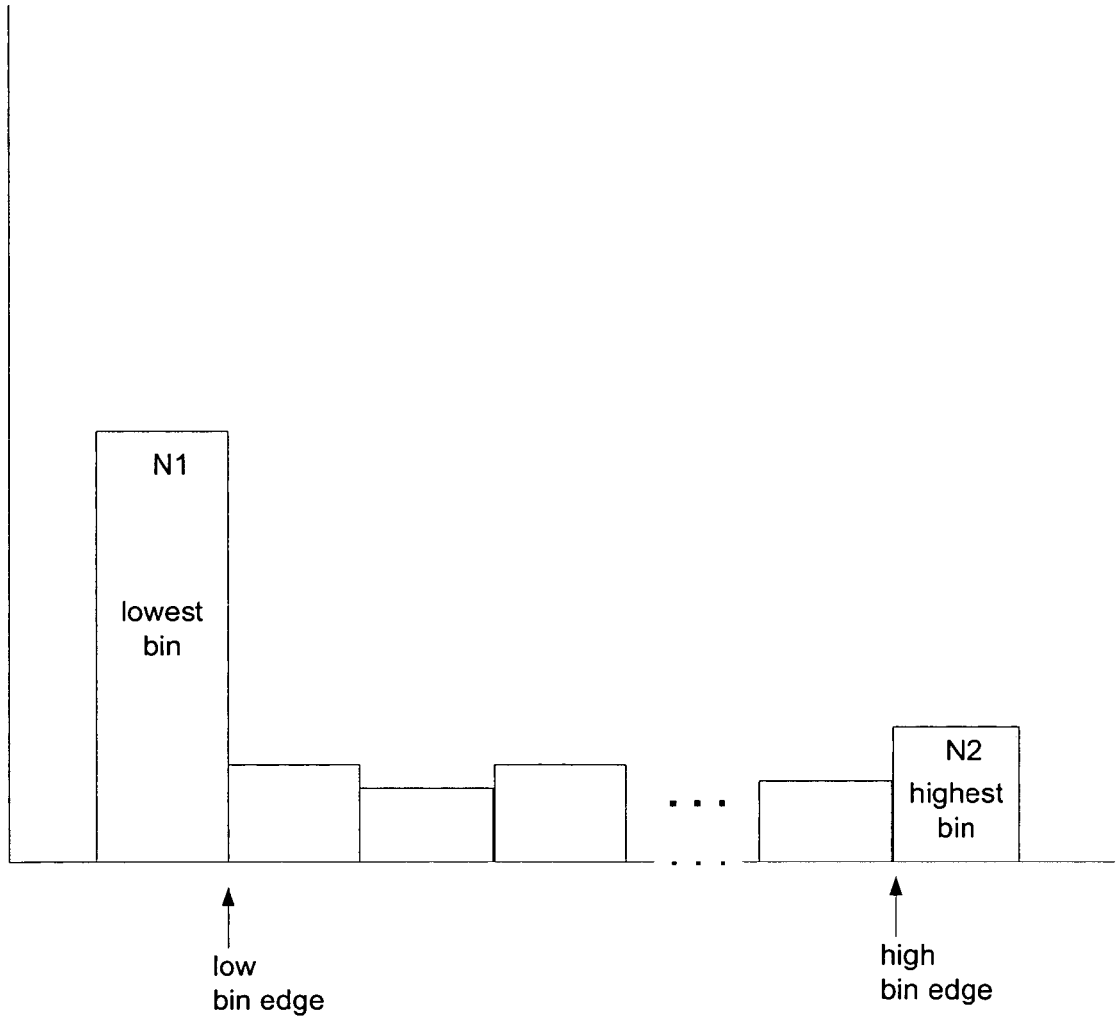
FIG. 13 illustrates an exemplary histogram which is useful for describing specific schemes for performing the step of updating parameters in the flow diagrams of FIGS. 11 and 12, in accordance with embodiments of the present invention.

In accordance with another embodiment for updating the parameters at step 1114, the low threshold $T_L$ and high threshold $T_H$ are fixed, and the bin edges for the lowest and highest bins ($B_L$ and $B_H$) are updated. That is, in this embodiment, the lowest bin edge $B_L$ and the highest bin edge $B_H$ are the variables that are determined at step 1114. When updating bin edges $B_L$ and $B_H$, the number of samples in the lowest bin and in the highest bin, $N_L$ and $N_H$, will change, thereby causing the ratio $N_L/N_H$ (or $N_H/N_L$) to change. This can be appreciated from the histogram shown in FIG. 13.

Figure 12:
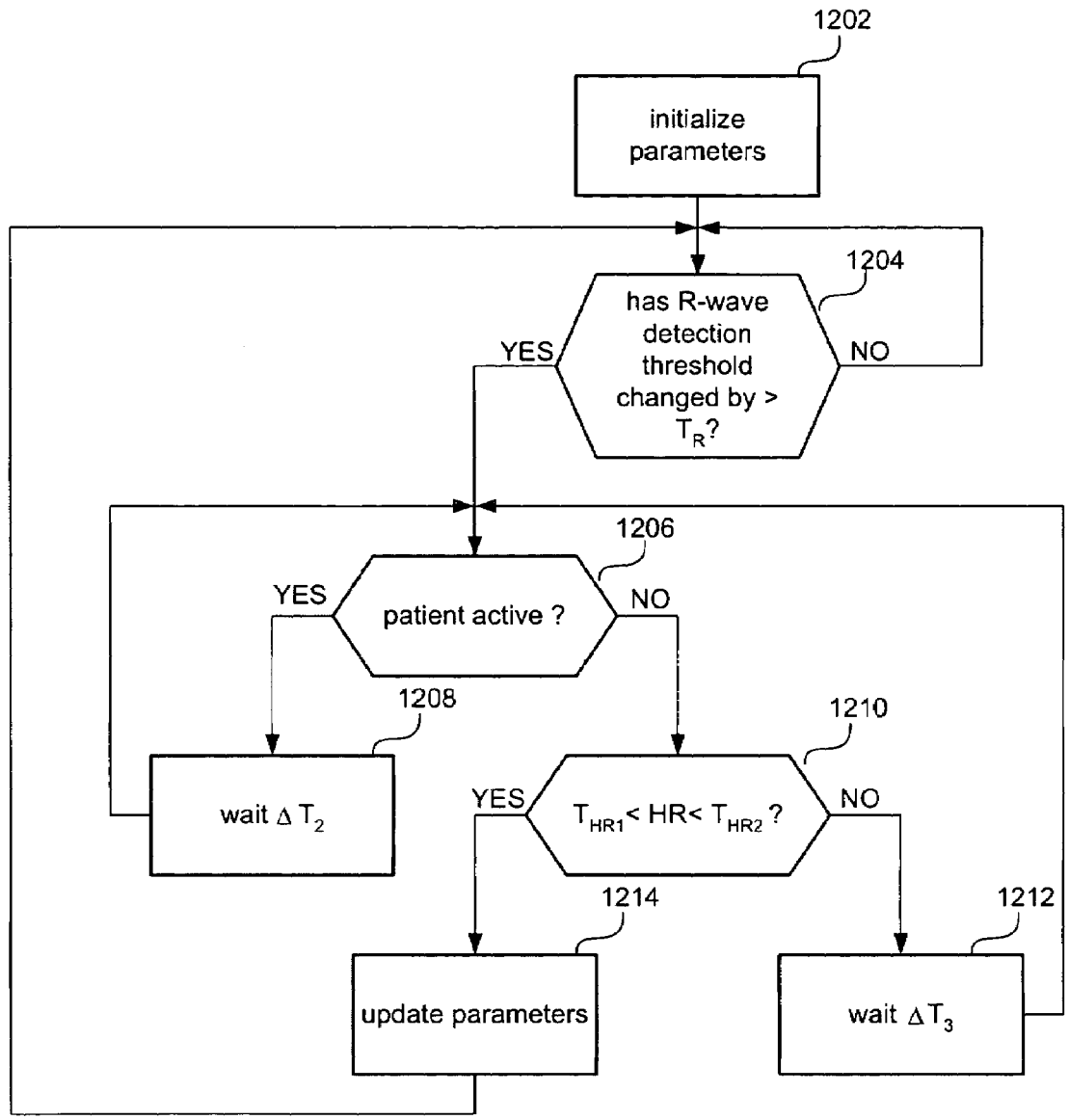
FIG. 12 is a high level flow diagram that is useful for describing how parameters used for myopotential detection can be updated in accordance with another embodiment of the present invention.

In accordance with another embodiment of the present invention, described with reference to FIG. 12, parameters are updated in response to the R-wave detection threshold changing by more than a specific amount $T_R$ (or the average R-wave amplitude changing by more than a specific amount). Referring to FIG. 12, at a step 1202, the parameters are initially programmed, in a similar manner as describe for step 1102. At a step 1204 there is a determination of whether the R-wave detection threshold has changed by more than a specific threshold amount ($T_R$) since the parameters were last updated (which can be when they were initialized). Embodiments in which an R-wave detection threshold is adjusted over time are discussed above with reference to FIGS. 5-8. Other schemes for adjusting an R-wave detection threshold are also possible and within the scope of step 1204. Step 1204 is repeated until the R-wave detection threshold changes by more than $T_R$, at which point flow goes to step 1206.

The determination at step 1204 can alternatively be whether the average R-wave amplitude has changed by more than a specific threshold. In such an embodiment, a running average for a sliding window (on the order of seconds, minutes, hours or days) can be continually determined.

The verification of lack of activity and acceptable heart rate range in steps 1206 through 1212 are similar to that in steps 1106 through 1112, and thus need not be described in further detail. Additionally, the updating of parameters at step 1214 is similar to the updating of parameters at step 1114.

In accordance with other embodiments of the present invention, an activity sensor is not used, causing flow to go directly from step 1104 to step 1110 in FIG. 11, and flow to go directly from step 1204 to step 1210 in FIG. 12. Such embodiments would be especially useful where an activity sensor is not available.

Now that various embodiments for detecting myopotential levels and R-waves have been described in detail, additional embodiments of the present invention that can use such information for detecting and discriminating between ventricular fibrillation (VF) and ventricular tachycardia (VT) shall be described.

Improved Detection of VT/VF from Remote Sensing Electrodes

As mentioned above, sensing cardiac electrical activity from electrodes spatially removed from the heart, as in a subQ extracardiac electrode configuration is challenging. This is because non-cardiac signals such as skeletal myopotentials and motion artifacts can easily be mistaken for an arrhythmia, which can lead to inappropriate therapy. Given the composite nature of subcutaneous signals, it is useful that a scheme for detecting non-cardiac events allow for changes (e.g., daily or hourly) in signal characteristics. The following embodiments of the present invention relate to improved systems and methods for detecting VT and VF arrhythmias from pairs of remote sensing electrodes, such as subQ extracardiac electrodes, examples of which were discussed above with reference to FIG. 1.

The following embodiments can utilize the myopotential detectors (e.g., 364) discussed above with reference to FIGS. 3, 9 and 10, the R-wave detectors (e.g., 362) discussed above with reference to FIGS. 3-8, and the activity/posture sensors and other non-cardiac parameter sensors (e.g., 118) discussed above with reference to FIGS. 1 and 3.

While the following description assumes the availability of two pairs of remote sensing electrodes, embodiments of the present invention can be applied to one or any number of electrode channels with slight modification. Furthermore, when more than one electrode pair is available, it is preferred that there is enough separation between each pair to reduce the amount of common myopotential seen by the pairs of electrodes. This is explained in further detail below.

Figure 14A:
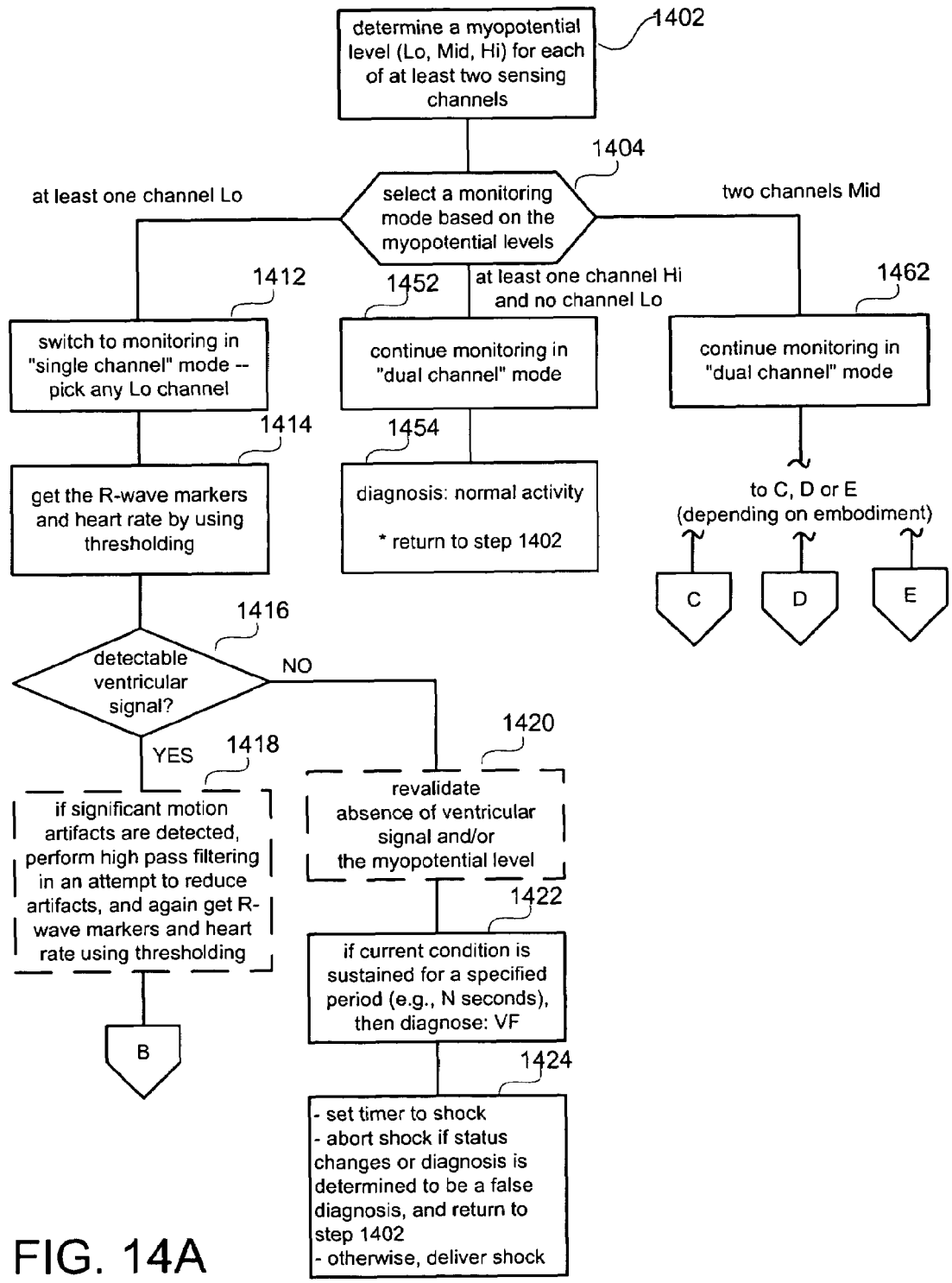
FIGS. 14A-14E are high level flow diagrams that are useful for describing embodiments of the present invention which relate to improved systems and methods for detecting VT and VF from remote sensing electrodes.

These embodiments of the present invention will now be described with reference to the high level flow diagram of FIGS. 14A-14E. Referring first to FIG. 14A, at a step 1402, the myopotential level is determined for each of at least two sensing channels, with each sensing channel corresponding to a sensing vector (defined by a pair of spaced apart electrodes of opposite polarity). In accordance with specific embodiments, this step includes classifying each channel as having either a "low" (Lo), "medium" (Mid) or "high" (Hi) myopotential level, e.g., as was described above in detail with reference to FIG. 9. Then, at a step 1404, a ventricular arrhythmia monitoring mode is selected based on the myopotential levels determined at step 1402.

More specifically, when the level of myopotential is determined to be "low" (Lo) in at least one sensing channel, the algorithm switches to a "single channel" mode at step 1412 (which is shown in the left branch in FIG. 14A), where only a single channel having low myopotential is monitored. If more than one of the channels is determined to have a low myopotential level, then one of these channels is selected for monitoring at step 1412. This can be accomplished, e.g., by designating one of the channels as a default channel that is to be selected if that channel and another channel both have a low myopotential level. In another embodiment, the channel having the lowest myopotential level is selected. These are just a few examples, which are not meant to be limiting.

When the level of myopotential is determined to be "high" (Hi) in at least one channel, and no channel has a "low" (Lo) myopotential level, (and there are not at least two channels with a "medium" (Mid) myopotential level) then the algorithm continues to monitor in "dual channel" mode at step 1452 (which is shown in the middle branch of FIG. 14A). At step 1452 at least two channels continue to be sensed, and it is assumed that the relatively high detected myopotential levels (at least one high, and no low) are due to normal patient activity, as indicated at step 1454. Flow then returns to step 1402.

When the myopotential level is determined to be "medium" (Mid) in at least two sensing channels, the algorithm continues to monitor in "dual channel" mode at step 1462 (which is shown in the right branch of FIG. 14A), where at least two channels continue to be sensed. As will be described further below, simultaneous match filtering or sliding window correlation can then be used on the two medium level myopotential channels, in an attempt to detect R-waves from the medium myopotential level channels. However, there will first be a complete discussion of the left branch of the flow diagram.

Returning to the discussion of the left branch of the flow diagram, after monitoring is switched to single channel mode at step 1412, then flow goes to step 1414 where thresholding is used to get R-wave markers and heart rate. Step 1414 can be performed, e.g., using any of the R-wave detection schemes discussed above with reference to FIGS. 4-8. As described above, the R-wave detection threshold can be a scalar value, e.g., determined as a percentage averaged R-wave amplitudes during rest. As also described above, the value of the R-wave detection threshold can be changed to automatically track signal trends and/or to adjust overall sensitivity. It is also within the scope of the present invention to change the R-wave detection threshold based on the amount of detected myopotential (e.g., the higher the myopotential, the higher the R-wave detection threshold).

Next, at a step 1416, there is a determination of whether a ventricular signal is detectable, based on the results of step 1414. This step can be performed based on whether there were detectable R-waves for a specified period of time (and thus, a detectable heart rate) at step 1414. If there were no detectable R-waves at step 1414 (or an abnormally low number of R-waves, or a HR less than a low threshold, e.g., 30 beats per minute), then at step 1416 it is assumed that there is no detectable ventricular signal, and thus, that the patient may be experiencing ventricular fibrillation (VF). The absence of detectable R-waves is optionally revalidated at step 1420, or flow continues to step 1422. Revalidation can be accomplished, e.g., by checking the power (absolute power or signal-to-noise ratio) of the signal received on the channel being monitored and comparing it to an appropriate threshold. Additionally, or alternatively, step 1420 can include revalidating that the myopotential level on that channel is still low. If presence of VF is not revalidated, then flow can return to step 1402.

If the present condition (i.e., absence of a detectable ventricular signal) is sustained for a specified period of time (e.g., N seconds), then there is a diagnosis at step 1422 that the patient is experiencing VF, otherwise (i.e., if the condition is not sustained) flow returns to step 1402. Then, at step 1424, preparation for delivering an appropriate shock is initiated (e.g., set timer to shock), while at the same time one or more non-cardiac parameter sensors (e.g., 118 in FIGS. 1 and 3) is preferably used to check for a false diagnosis or whether there is a change in the patient's status. For example, pulse pressure information, activity information, posture information and/or respiratory information can be obtained at step 1424 using one or more non-cardiac parameter sensors 118 (discussed above with reference to FIGS. 1 and 3), and such information can be compared to appropriate thresholds to confirm or not confirm the VF diagnosis. More specifically, if the patient is experiencing VF, pulse pressure should significantly drop, the patient should not be active (e.g., walking), the patient should not be standing up or sitting up, and respiration should significantly drop or cease. If there is a determination at step 1424 that there was a false diagnosis of VF or that the patient's status is now stable, then the delivery of the shock is aborted, otherwise shock therapy is delivered.

Figure 14B:
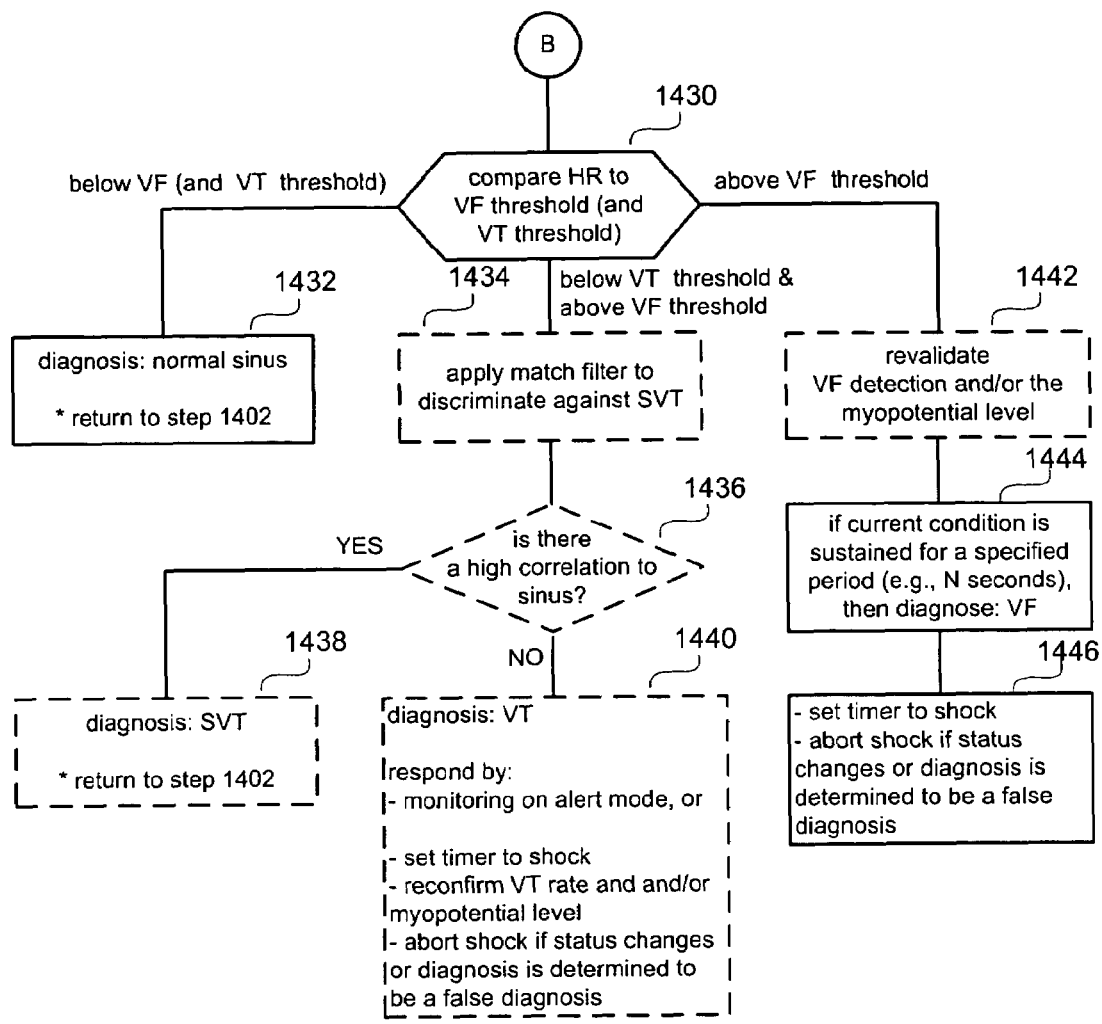

Returning to step 1416, if there is a detectible ventricular signal, then flow goes to optional step 1418, or directly to step 1430, shown in FIG. 14B. At step 1418, if an activity sensor (examples of which are discussed above) indicates significant activity, and thus that motion artifacts are likely present, then high pass filtering can be used to reduce motion artifacts, and R-waves/heart rate are again detected in a similar manner as was discussed with reference to step 1414. Additional details of motion artifact removal (MAR) methods and units are described in detail above. Next, at a step 1430, shown in FIG. 14B, the detected heart rate is compared to at least a VF threshold (and optionally also a VT threshold, with the VF threshold being greater than the VT threshold). If the heart rate is below the VF threshold (and below the VT threshold), then flow goes to step 1432 where there is a diagnosis that the patient is in normal sinus rhythm. At this point flow can return to step 1402.

If the heart rate is above the VF threshold then flow goes to optional step 1442, or directly to step 1444. At step 1442, the VF detection is revalidated. Such revalidation can be accomplished, e.g., by checking the power (absolute power or signal-to-noise ratio) of the signal received on the channel being monitored and comparing it to an appropriate threshold. This step may also include revalidating that the myopotential level on that channel has not changed. If presence of VF is not revalidated, then flow can return to step 1402.

If the present condition (i.e., HR>VF threshold) is sustained for a specified period of time (e.g., N seconds), then there is a diagnosis at step 1444 that the patient is experiencing VF, otherwise (i.e., if the condition is not sustained) flow returns to step 1402. Then, at step 1446, after a VF diagnosis, preparation for delivering an appropriate shock is initiated (e.g., set timer to shock), while at the same time one or more non-cardiac parameter sensors (e.g., 118, in FIGS. 1 and 3) is preferably used to check for a false diagnosis or whether there is a change in the patient's status, in a similar manner to that explained with reference to step 1424. For example, pulse pressure information, activity information, posture information and/or respiratory information can be obtained at step 1446 using one or more non-cardiac parameter sensor, and such information can be compared to appropriate thresholds to confirm or not confirm the VF diagnosis. If there is a determination at step 1446 that there was a false diagnosis of VF or that the patient's status is now stable, then the delivery of the shock is aborted, otherwise shock therapy is delivered.

Optionally, if it is determined at step 1430 that the patient's heart rate is greater than the VT threshold, but less than the VF threshold (i.e., VT threshold<HR<VF threshold), then flow can go to step 1434 where a match filter is applied to discriminate against supraventricular (originating above the ventricles) tachycardia (SVT), which is a series of fast atrial heartbeats that can be uncomfortable and frightening, but does not require shock treatment. Such match filtering can include comparing the present cardiac signal to a stored cardiac signal that is indicative of normal sinus rhythm, such that a correlation between the present signal and the stored signal can be determined, and, e.g., compared to an appropriate correlation threshold. If there is determined to be a high correlation to normal sinus rhythm at step 1436, flow goes to step 1438 where there is a SVT diagnosis. At this point flow can return to step 1402.

If it is determined at step 1436 that there is not a high correlation between the match filter and the sensed signal, then there is a VT diagnosis at step 1440. At this point, the device can respond by monitoring on alert mode, which can include increasing sensitivity to detecting VF (in case the patient goes from VT to VF). Alternatively, at this point preparation for delivering an appropriate shock can be initiated (e.g., set timer to shock), while at the same time there is preferably a check as to whether the myopotential level has changed, and/or whether the HR is still between the VT threshold and the VF threshold. If myopotential level has changed and/or if the HR is no longer between the VT threshold and VF threshold, then flow goes back to 1402. If myopotential level has not changed and HR is still between VT and VF threshold, then anti VT shock therapy can be delivered at step 1440. It is also possible that one or more non-cardiac parameter sensors can be used to check for a false diagnosis or whether there is a change in the patient's status, as was discussed above with regards to step 1424. If there is a determination at step 1440 that there was a false diagnosis of VT or that the patient's status is now stable, then the delivery of the shock can be aborted, and flow can return to step 1402. Otherwise, the shock is delivered.

Returning to the right branch in FIG. 14A, as was mentioned above, if two channels are found to have a "medium" (Mid) myopotential level, then those two channels having medium myopotential continue to be monitored, as indicated at step 1462. Depending on the embodiment implemented, flow can then go to step 1464 in FIG. 14C, to step 1474 in FIG. 14D, or to step 1490 in FIG. 14E. In other words, FIGS. 14C, 14D and 14E describe three alternative embodiments for proceeding once it is determined that two channels have medium myopotential levels. The embodiment of FIG. 14C will be discussed first, followed by the embodiment of FIG. 14D, and then the embodiment of FIG. 14E.

Figure 14C:
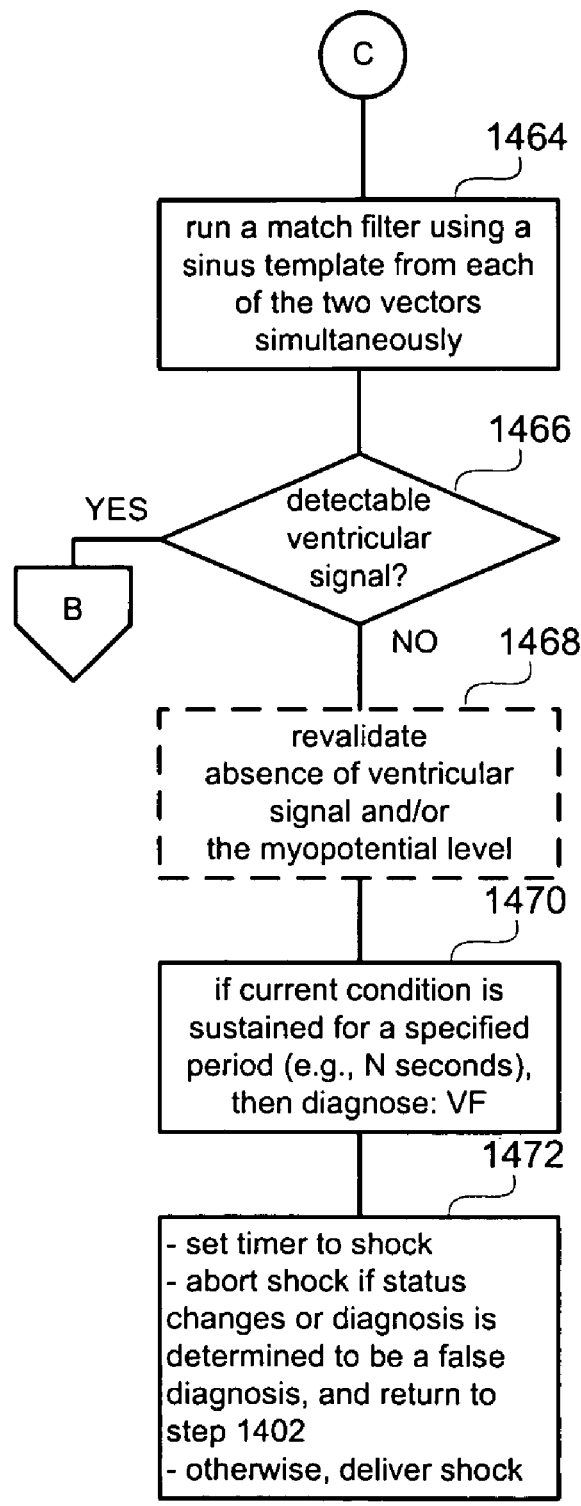

Referring now to the embodiment of FIG. 14C, at a step 1464, match filtering is performed using a template from each of the two channels/vectors, such that an R-wave is detected when both filters indicate a match to their own sinus template. Such match filtering can include comparing the present cardiac signal sensed by each channel/vector to a corresponding stored cardiac signal that is indicative of normal sinus rhythm as sensed by that channel/vector, such that a high correlation between the present signal and the stored signal can be detected. Preferably, step 1464 is performed using a low pass filtered version of the signals, which should yield better results.

Next, at step 1466, there is a determination of whether there is a detectable ventricular signal in any of the channels being monitored, based on the results of step 1464. For example, this step can be performed based on whether there were detectable R-waves in at least one of the channels for a specified period of time (and thus, a detectable heart rate) at step 1464. If there was determined to be a detectable ventricular signal in at least one of the channels, then flow goes to step 1430 of FIG. 14B, which was described in detail above. If there were no detectable R-waves in any of the channels being monitored at step 1464 (or an abnormally low number of R-waves, or a HR less than a low threshold, e.g., 30 beats per minute), then at step 1466 it is assumed that there is no detectable ventricular signal, and thus, that the patient may be experiencing ventricular fibrillation (VF). The absence of detectable R-waves and/or the myopotential levels are optionally revalidated at step 1468, in a similar manner as done at step 1420 (of FIG. 14A). If there is no revalidation, then flow can return to step 1402.

If the current condition (i.e., no detectable ventricular signal in any channel) is sustained for a specified period (e.g., N seconds), then there is a VF diagnosis at step 1470. Then, at step 1472, preparation for delivering a shock is initiated (e.g., set timer to shock), while at the same time one or more non-cardiac parameter sensors is preferably used to check for a false diagnosis or whether there is a change in the patient's status, in a similar manner as was explained above with reference to step 1424 (of FIG. 14A). If there is a determination at step 1472 that there was a false diagnosis of VF or that the patient's status is now stable, then the delivery of the shock can be aborted. Otherwise, appropriate shock therapy is delivered at step 1472.

Figure 14D:
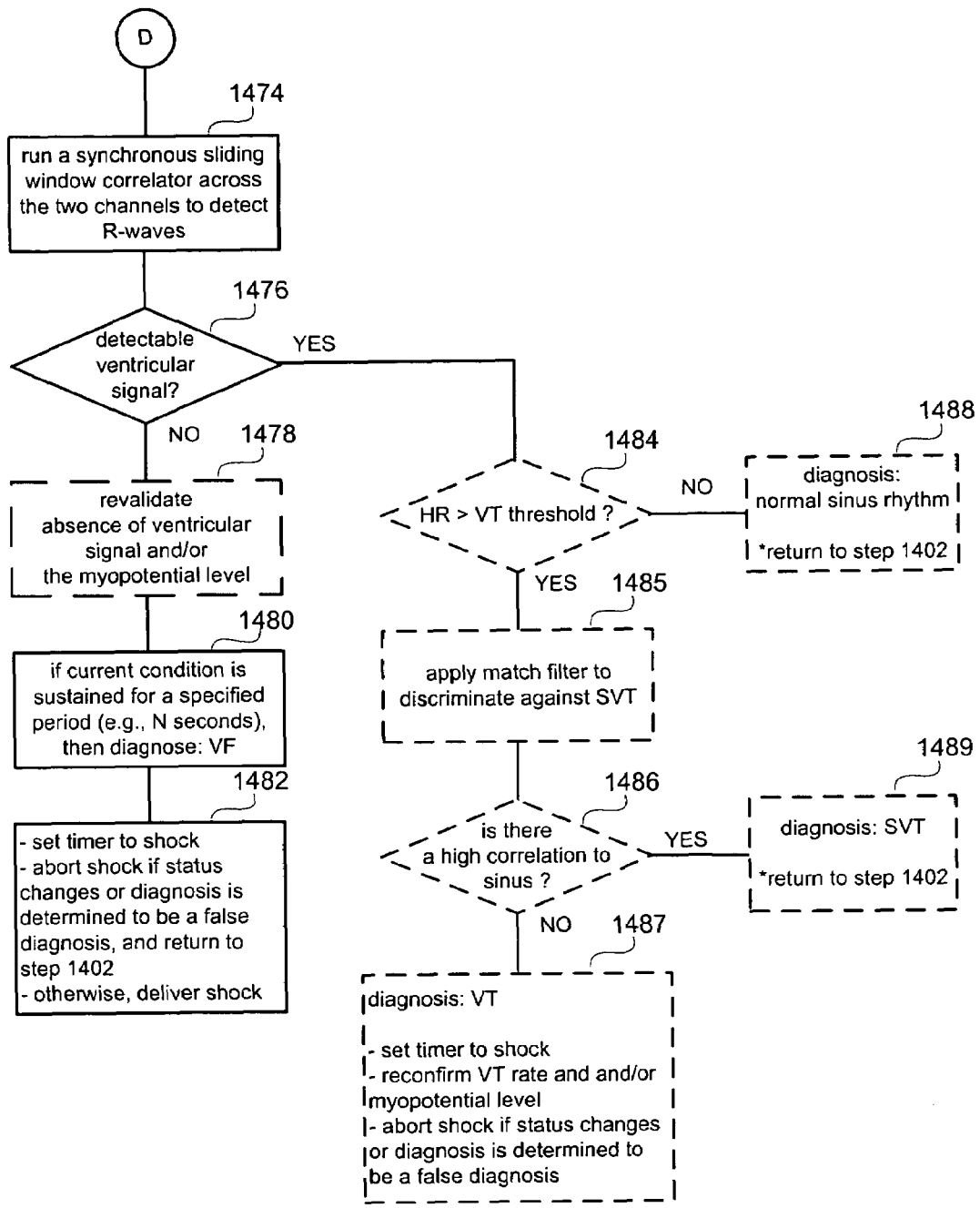

Referring now to the embodiment of FIG. 14D, at a step 1474, a sliding correlation window between the two channels (that are determined to have a medium level of myopotential) is used, such that R-waves can be detected when the two signals are highly correlated (e.g., as defined by a correlation threshold). Preferably, step 1474 is performed using a low pass filtered version of the signals, which should yield better results. Then, at step 1476 there is a determination of whether there is a detectable ventricular signal, based on the results of step 1474. This step is similar to steps 1416 and 1466 discussed above, and thus, need not be explained again in detail. If there is determined to be no detectable ventricular signal, then revalidation of the absence of the ventricular signal and/or the level of myopotential can optionally be performed at step 1478, in a similar manner as was discussed above with reference to steps 1420 and 1468. If there is no revalidation, then flow can return to step 1402.

Next, at step 1480, if the current condition (i.e., no detectable ventricular signal) is sustained for a specified period of time (e.g., N seconds), then there is a VF diagnosis. Then, at step 1482, preparation for delivering a shock is initiated (e.g., set timer to shock), while at the same time one or more non-cardiac parameter sensor is preferably used to check for a false diagnosis or whether there is a change in the patient's status, in a similar manner as was explained above with reference to step 1424 (of FIG. 14A). If there is a determination at step 1482 that there was a false diagnosis of VF or that the patient's status is now stable, then the delivery of the shock can be aborted. Otherwise, appropriate shock therapy is delivered at step 1482.

Returning to step 1476, if there is a detectable ventricular signal, then flow goes to optional step 1484 (or immediately back to step 1402, if optional step 1484 is not performed). At step 1484, there is a determination of whether the patient's heart rate (HR) is greater than the VT threshold. If the heart rate is not greater than the VT threshold, then there is a diagnosis of normal sinus rhythm at step 1488. If the heart rate is greater than the VT threshold, then a match filter is applied to discriminate against SVT at step 1485, in a similar manner as at step 1434 (of FIG. 14B) described above. Such match filtering can include comparing the present cardiac signal to a stored cardiac signal that is indicative of normal sinus rhythm, such that a correlation between the present signal and the stored signal can be determined. If there is determined to be a high correlation to normal sinus rhythm at step 1486, flow goes to step 1489 where there is a SVT diagnosis. At this point flow can return to step 1402. If there is not a high correlation, then flow goes to step 1487, and preparation for delivering an appropriate shock can be initiated (e.g., set timer to shock), while at the same time there is preferably a check as to whether the myopotential level has changed, and/or a check whether the HR is still above the VT threshold. If myopotential level has changed and/or the HR is no longer above the VT threshold, then flow goes back to 1402. If myopotential level has not changed and HR is still above the VT threshold, then anti VT shock therapy can be delivered. It is also possible that one or more non-cardiac parameter sensors can be used to check for a false diagnosis or for a change in the patient's status, as was discussed above with regards to step 1424. If there is a determination at step 1489 that there was a false diagnosis of VT or that the patient's status is now stable, then the delivery of the shock can be aborted.

Figure 14E:
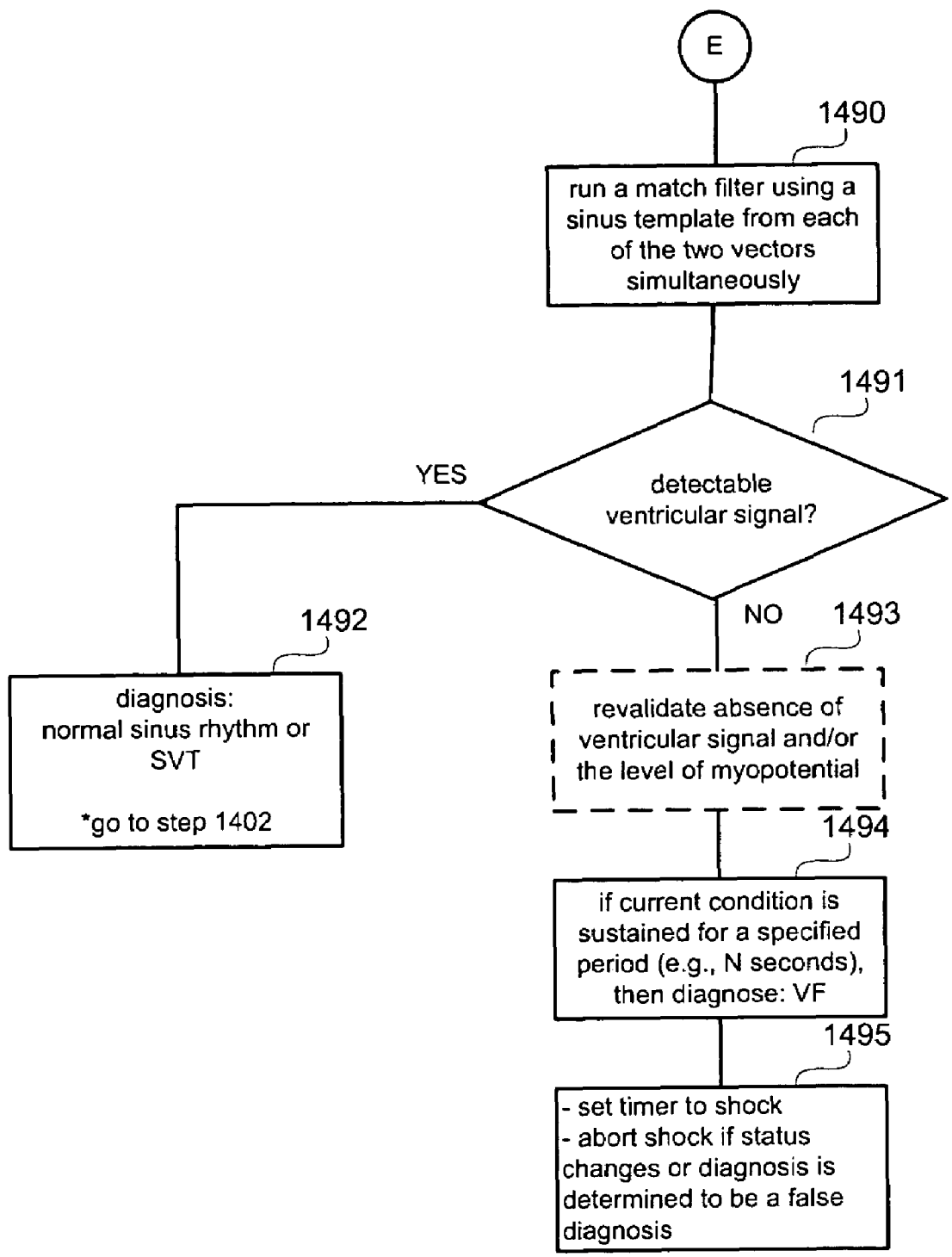

Referring now to the embodiment of FIG. 14E, at step 1490, match filtering is performed using a template from each of the two channels/vectors, such that an R-wave is detected when both filters indicate a match to their own sinus template, in a similar manner as was described above for step 1464 (of FIG. 14C). Next, at step 1491, there is a determination of whether there is a detectable ventricular signal in any of the channels being monitored, based on the results of step 1490, in a similar manner as was described with reference to step 1466 (of FIG. 14C). If there is determined to be a detectable ventricular signal at step 1491, then flow goes to step 1492 where there is a normal sinus rhythm or SVT diagnosis. At this point flow can return to step 1402. If there is not determined to be a detectable ventricular signal at step 1491, then flow goes to step 1493. Steps 1493, 1494 and 1495 are similar, respectively, to steps 1468, 1470 and 1472 discussed above with reference to FIG. 14C, and thus need not be described again.

In embodiments where the myopotential detector is used to determine whether myopotential is absent or present in each sensing channel, a single channel ventricular arrhythmia monitoring mode (in which a channel where myopotential is absent is selected for ventricular arrhythmia monitoring) is selected, if myopotential is determined to be absent in at least one of the sensing channels. If myopotential is determined to be present in all of the sensing channels, then a multi-channel ventricular arrhythmia monitoring mode (in which at least two of the sensing channels are selected for ventricular arrhythmia monitoring) is selected.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

What is claimed is:

1. In an implantable system, a method for performing ventricular arrhythmia monitoring comprising:
    (a) monitoring skeletal muscle myopotential associated with at least two sensing channels, each of which is associated with a different sensing vector, each sensing vector defined by a different pair of spaced apart electrodes, and determining a myopotential level for each of the sensing channels, wherein the myopotential level may be one of a low, medium and high myopotential level;
    (b) selecting one of a dual-channel or a single-channel ventricular arrhythmia monitoring mode based on the determined myopotential levels; and
    (c) performing ventricular arrhythmia monitoring using the selected monitoring mode.

2. In an implantable system, a method for performing ventricular arrhythmia monitoring comprising:
    (a) monitoring myopotential associated with each of at least two sensing channels, each of which is associated with a different sensing vector, each sensing vector defined by a different pair of spaced apart electrodes, and determining a myopotential level for each of the sensing channels;
    (b) selecting a ventricular arrhythmia monitoring mode based on the determined myopotential levels; and
    (c) performing ventricular arrhythmia monitoring using the selected monitoring mode;
    wherein step (b) comprises:
    if at least one of the sensing channels is determined to have a low myopotential level, then selecting a single channel ventricular arrhythmia monitoring mode in which a single channel having a low myopotential level is selected for monitoring; and
    if none of the sensing channels are determined to have a low myopotential level, then selecting a dual channel ventricular arrhythmia monitoring mode in which two of the sensing channels are selected for monitoring.

3. The method of claim 2, wherein, if a single channel ventricular arrhythmia monitoring mode is selected at step (b), then step (c) comprises:
    performing thresholding to detect R-waves and a heart rate in the single channel that is selected for monitoring;
    making an initial diagnosis using results of the thresholding.

4. In an implantable system, a method for performing ventricular arrhythmia monitoring comprising:

(a) monitoring myopotential associated with each of at least two sensing channels, each of which is associated with a different sensing vector, each sensing vector defined by a different pair of spaced apart electrodes, and determining a myopotential level for each of the sensing channels;
(b) selecting a ventricular arrhythmia monitoring mode based on the determined myopotential levels;
(c) performing ventricular arrhythmia monitoring using the selected monitoring mode;
wherein, if a dual channel ventricular arrhythmia monitoring mode is selected at step (b), and two of the sensing channels are determined to have a medium myopotential level, then step (c) comprises:
performing simultaneous match filtering in each of the two sensing channels having a medium myopotential level, by running a match filter using a previously stored sinus template associated with the channel, such that an R-wave is detected when the match filters for the two sensing channels both indicate a match to their own previously stored sinus template; and
making an initial diagnosis using results of the simultaneous match filtering.

5. The method of claim 4, further comprising:
(d) if a ventricular arrhythmia treatable by a shock is diagnosed at step (c), then using a non-cardiac parameter sensor to check for a false initial diagnosis before delivering the shock.

6. An implantable system for performing ventricular arrhythmia monitoring using at least two sensing channels that are each associated with different sensing vectors, comprising:
a myopotential detector to monitor skeletal muscle myopotential associated with each of the sensing channels; and
an arrhythmia monitor to select one of a dual-channel or a single-channel ventricular arrhythmia monitoring mode based on the monitored myopotential, and to perform ventricular arrhythmia monitoring using the selected monitoring mode;
wherein the myopotential detector assigns each sensing channel one of a low, medium and high myopotential level.

7. The system of claim 6, wherein the different sensing vectors are defined by extracardiac remote sensing electrodes that are subcutaneously implanted in a patient.

8. An implantable system for performing ventricular arrhythmia monitoring using at least two sensing channels that are each associated with different sensing vectors, comprising:
a myopotential detector to monitor myopotential associated with each of the sensing channels; and
an arrhythmia monitor to select a ventricular arrhythmia monitoring mode based on the monitored myopotential, and to perform ventricular arrhythmia monitoring using the selected monitoring mode;
wherein the monitor:
selects a single channel ventricular arrhythmia monitoring mode in which a single channel having a low myopotential level is selected for monitoring, if at least one of the sensing channels is determined to have a low myopotential level; and
selects a dual channel ventricular arrhythmia monitoring mode in which two of the sensing channels are selected for monitoring, if none of the sensing channels are determined to have a low myopotential level.

9. The system of claim 8, wherein, if the monitor selects a single channel ventricular arrhythmia monitoring mode, then the monitor performs thresholding to detect R-waves and a heart rate in the single channel that is selected for monitoring, and the monitor makes an initial diagnosis using results of the thresholding.

\* \* \* \* \*